(12) United States Patent
Laakso et al.

(10) Patent No.: US 10,939,970 B2
(45) Date of Patent: Mar. 9, 2021

(54) ROBOTIC SURGERY SYSTEM

(71) Applicant: Titan Medical Inc., Toronto (CA)

(72) Inventors: Aki Hannu Einari Laakso, Raleigh, NC (US); Hans Christian Pflaumer, Apex, NC (US); Abraham Allen Shipley, Apex, NC (US); Nathan Wagner Ginsberg, Ashby, MA (US); Yahia Laouar, Superior, CO (US); Cara Lee Coad, Longmont, CO (US); Michael James Ross, Thornton, CO (US); John Michael Burton, Jr., Charleston, SC (US)

(73) Assignee: Titan Medical Inc., Toronto (CA)

( * ) Notice: Subject to any disclaimer, the term of this patent is extended or adjusted under 35 U.S.C. 154(b) by 0 days.

(21) Appl. No.: 16/419,696

(22) Filed: May 22, 2019

(65) Prior Publication Data

US 2020/0367979 A1 Nov. 26, 2020

(51) Int. Cl.
*A61B 34/30* (2016.01)
*A61B 90/50* (2016.01)
*A61B 34/00* (2016.01)

(52) U.S. Cl.
CPC .............. *A61B 34/30* (2016.02); *A61B 34/71* (2016.02); *A61B 34/74* (2016.02); *A61B 90/50* (2016.02)

(58) Field of Classification Search
CPC ... A61B 1/0016; A61B 1/00133; A61B 34/30; A61B 34/71; A61B 34/74; A61B 90/50
See application file for complete search history.

(56) References Cited

U.S. PATENT DOCUMENTS

| 5,553,198 A | 9/1996 | Wang et al. |
| 6,491,701 B2 | 12/2002 | Tierney et al. |

(Continued)

FOREIGN PATENT DOCUMENTS

| CA | 2 547 686 | 8/1997 |

OTHER PUBLICATIONS

Titan Medical SPORT Surgical System, https://web.archive.org/web/20180326233829/https://titanmedicalinc.com/technology/, available before May 22, 2018.

(Continued)

*Primary Examiner* — Prasad V Gokhale
(74) *Attorney, Agent, or Firm* — Knobbe, Martens, Olson & Bear LLP

(57) ABSTRACT

A robotic surgery system includes a control unit assembly that supports and operates one or more robotic tools and a mechanical arm assembly that movably supports the control unit assembly in space. The mechanical arm assembly includes a boom assembly with one or more boom arms rotatably coupled to each other via one or more joints and having one or more actuators. An elevating linkage assembly is coupled to the boom assembly and has an actuator operable to allow vertical movement of the control unit assembly in a substantially weightless manner. Yaw and pitch control assemblies are interposed between the elevating linkage assembly and the control unit assembly and have actuators operable to allow movement of the control unit assembly in yaw and pitch. The one or more actuators are actuatable to allow movement of the control unit assembly in space upon actuation of one or more user interfaces of the control unit assembly.

23 Claims, 24 Drawing Sheets

(56) References Cited

U.S. PATENT DOCUMENTS

| | | | |
|---|---|---|---|
| 6,685,698 B2 | 2/2004 | Morley et al. | |
| 6,793,653 B2 | 9/2004 | Sanchez et al. | |
| 7,074,179 B2 | 7/2006 | Wang et al. | |
| 7,122,707 B2 | 10/2006 | Petzoldt et al. | |
| 7,914,521 B2 | 3/2011 | Wang et al. | |
| 8,142,447 B2 | 3/2012 | Cooper et al. | |
| 8,241,271 B2 | 8/2012 | Millman et al. | |
| 8,638,057 B2 | 1/2014 | Goldberg et al. | |
| 9,707,684 B2 * | 7/2017 | Ruiz Morales | A61B 34/70 |
| 10,058,396 B1 | 8/2018 | Genova et al. | |
| 10,245,113 B1 | 4/2019 | Genova et al. | |
| 10,398,287 B1 | 9/2019 | Genova | |
| 2010/0069920 A1 * | 3/2010 | Naylor | A61B 34/71 |
| | | | 606/130 |
| 2014/0230595 A1 | 8/2014 | Butt et al. | |
| 2014/0249546 A1 | 9/2014 | Shvartsberg et al. | |
| 2016/0073978 A1 * | 3/2016 | Henderson | A61B 6/0487 |
| | | | 5/600 |
| 2016/0143633 A1 | 5/2016 | Robert et al. | |
| 2017/0312047 A1 * | 11/2017 | Swarup | A61B 34/30 |
| 2018/0256259 A1 * | 9/2018 | Crawford | A61B 6/5217 |
| 2018/0353245 A1 | 12/2018 | Mccloud et al. | |
| 2018/0353254 A1 | 12/2018 | Lutzow et al. | |
| 2019/0060029 A1 | 2/2019 | Kralicky | |
| 2019/0082931 A1 | 3/2019 | Andrews et al. | |
| 2019/0187741 A1 | 6/2019 | Walters et al. | |

OTHER PUBLICATIONS

Titan Medical SPORT Surgical System, https://web.archive.org/web/20190328045351/https://titanmedicalinc.com/technology/, available before May 22, 2019.

\* cited by examiner

ROBOTIC SURGERY SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND

Field

The present disclosure generally relates to robotic surgical systems, and more particularly to mechanisms for moving a mechanical arm assembly and control unit assembly of a robotic surgical system.

Description of the Related Art

Robotic surgery systems generally include an operator interface that receives operator input from a surgeon and causes corresponding movements of surgical tools within a body cavity of a patient to perform a surgical procedure. The operator interface can be on a workstation that the surgeon interfaces with to perform a surgical procedure using the surgical tools. The surgical tools can be on a cart separate from the workstation. The cart can be mobile, allowing hospital staff to move the cart into an operating room prior to the surgical procedure, and to remove it from the operating room once the surgical procedure has been completed.

SUMMARY

In accordance with one aspect of the disclosure, a robotic surgical system is provided with a control unit assembly that supports and operates one or more robotic tools and a mechanical arm assembly that movably supports the control unit assembly in space. The mechanical arm assembly selectively allows movement of the control unit assembly in space (e.g., in a space defined by Cartesian coordinates, as well as in pitch and yaw) upon actuation of one or more actuators of the mechanical arm assembly to allow manual movement of the control unit assembly.

In accordance with another aspect of the disclosure, a robotic surgical system is provided with a control unit assembly that supports and operates one or more robotic tools and a mechanical arm assembly that movably supports the control unit assembly in space. The mechanical arm assembly selectively allows movement of the control unit assembly in space (e.g., in a space defined by Cartesian coordinates, as well as in pitch and yaw) upon actuation of one or more brakes (e.g., electromagnetic brakes) of the mechanical arm assembly to allow manual movement of the control unit assembly.

In accordance with another aspect of the disclosure, manual movement of the control unit assembly is effected by an operator by engaging one or more (e.g., at least two) user interfaces on the control unit assembly to unlock movement of the control unit assembly in space. Optionally, the user interfaces are depressible buttons. In another implementation, the user interfaces are tactile sensors. Optionally, one or more of the user interfaces are disposed at or proximate corners of the control unit assembly.

In accordance with another aspect of the disclosure, a boom assembly of the mechanical arm assembly can include one or more boom arms pivotable relative to each other about a joint, and have an actuator (e.g., brake) disposed about an axis of the joint. The actuator is operable to allow or disallow relative movement of the one or more boom arms.

In accordance with another aspect of the disclosure, an elevating linkage assembly of the mechanical arm assembly selectively allows vertical movement of the control unit assembly in a substantially weightless manner via movement of a pylon that is counterbalanced by compression of a spring. The pylon and spring are coupled by a cable that extends over and engages a pulley such that a weight exerted on the pylon by the control unit assembly is substantially equal to the spring compression force.

In accordance with another aspect of the disclosure, a yaw control assembly of the mechanical arm assembly selectively allows movement of the control unit assembly in a yaw direction, and has an actuator (e.g., brake) disposed about an axis of the yaw control assembly. The actuator is operable to allow or disallow movement of the control unit assembly in yaw.

In accordance with another aspect of the disclosure, a pitch control assembly of the mechanical arm assembly selectively allows movement of the control unit assembly in a pitch direction, and has one or more actuators (e.g., brakes) disposed about an axis of the pitch control assembly, the actuator(s) being operable to allow or disallow movement of the control unit assembly in pitch.

In accordance with another aspect of the disclosure, the control unit assembly has a counterbalance assembly operatively coupled to the pitch control assembly to counterbalance at least a portion of the weight of the control unit assembly when it is moved in a pitch direction to allow pitch movement in a weightless manner.

In accordance with another aspect of the disclosure, a robotic surgery system is provided. The system comprises a control unit assembly configured to support and operate one or more robotic tools, and a mechanical arm assembly configured to movably support the control unit assembly in space. The mechanical arm assembly comprises a pillar assembly extending along a first axis, and a boom assembly movably coupled to the pillar assembly and extending generally perpendicular to the first axis. The boom assembly comprises a proximal boom arm rotatably coupled to the pillar assembly via a first joint and a distal boom arm rotatably coupled to the proximal boom arm via a second joint, and one or more brakes arranged about one or both of the first and second joints. The mechanical arm assembly also comprises an elevating linkage assembly coupled to the distal boom arm and extending along a second axis generally parallel to the first axis. The elevating linkage assembly is disposed above and operatively coupled to the control unit assembly. The elevating linkage assembly comprises a brake operable to allow vertical movement of the control unit assembly relative to the boom assembly in a substantially weightless manner. The mechanical arm assembly also comprises a pitch and yaw assembly disposed between the control unit assembly and the elevating linkage assembly and configured to allow movement of the control unit assembly in one or both of a pitch direction and a yaw direction. The pitch and yaw assembly comprises one or more brakes operable to substantially brake movement of the control unit assembly in one or both of pitch and yaw. One or more of the brakes in the boom assembly, elevating linkage assembly and pitch and yaw assembly are actuatable between an unlocked position and a locked position, wherein the unlocked position allows an operator to manually change one or both of a position and an orientation of the control unit assembly in space, and wherein the locked position fixes the position and orientation of the control unit assembly in space.

In accordance with another aspect of the disclosure, a robotic surgery system is provided. The system comprises a control unit assembly configured to support and operate one or more robotic tools, and a mechanical arm assembly configured to movably support the control unit assembly in space. The mechanical arm assembly comprises a boom assembly comprising one or more boom arms rotatably coupled to each other via one or more joints, one or more actuators being arranged about the one or more joints and operable to allow movement of the one or more boom arms. The mechanical arm assembly also comprises an elevating linkage assembly coupled to the boom assembly and extending along an axis generally perpendicular to the boom assembly. The elevating linkage assembly is disposed above the control unit assembly and comprises an actuator operable to allow movement of the control unit assembly along the axis and relative to the boom assembly in a substantially weightless manner. The mechanical arm assembly also comprises a yaw control assembly disposed below the elevating linkage assembly and above the control unit assembly, the yaw control assembly comprising an actuator operable to allow movement of the control unit assembly in a yaw direction. The mechanical arm assembly also comprises a pitch control assembly disposed below the elevating linkage assembly and above the control unit assembly, the pitch control assembly comprising one or more actuators operable to allow movement of the control unit assembly in a pitch direction. One or more of the actuators in the boom assembly, elevating linkage assembly, yaw control assembly and pitch control assembly are actuatable to allow a change in one or both of a position and an orientation of the control unit assembly in space upon actuation of two or more user interfaces of the control unit assembly. One or more of the actuators in the boom assembly, elevating linkage assembly, yaw control assembly and pitch control assembly lock one or both of the position and the orientation of the control unit assembly when the user interfaces are not engaged.

DETAILED DESCRIPTION

Overview of Robotic Surgery System

Figure 1:
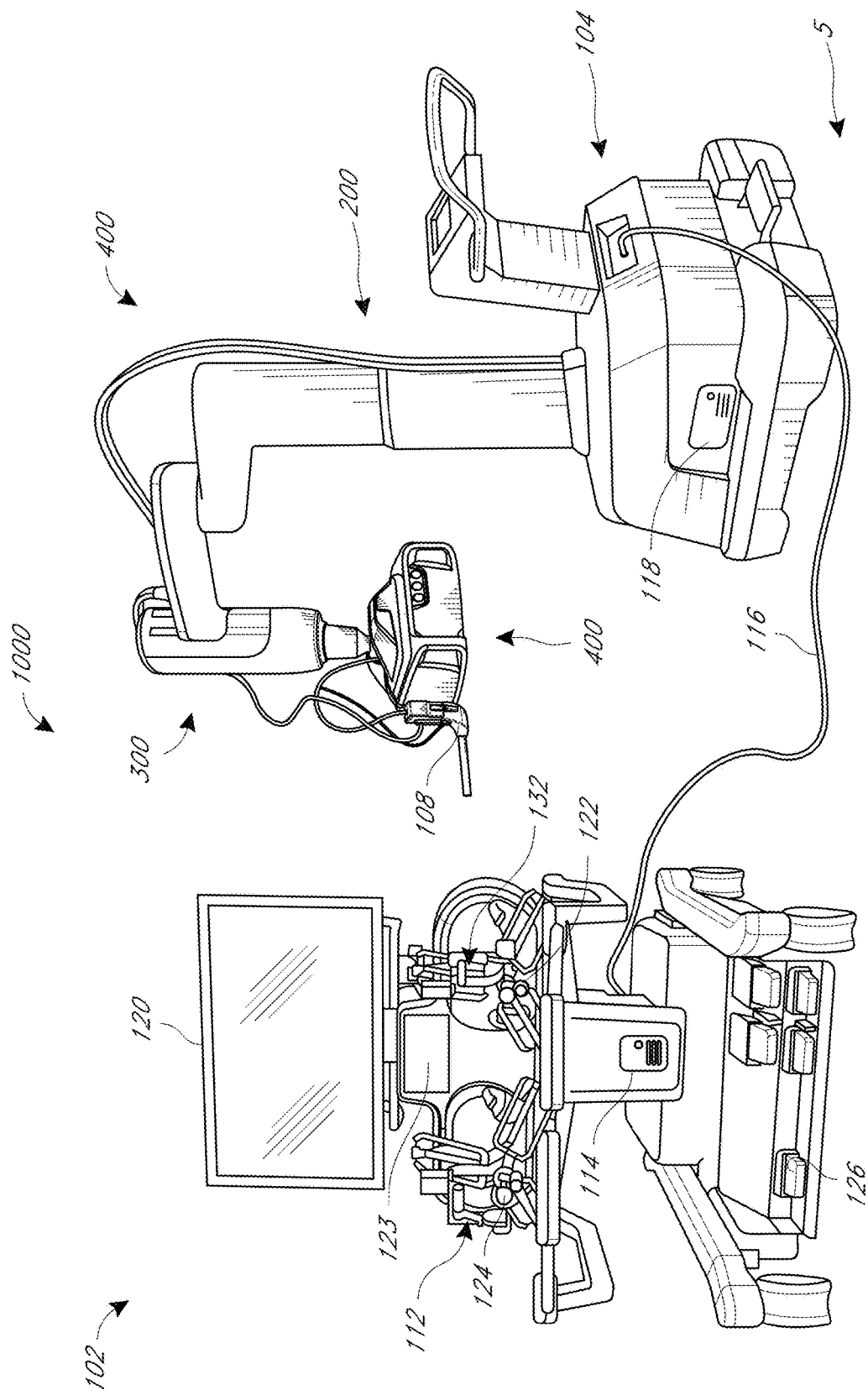
FIG. 1 illustrates a robotic surgery system.

FIG. 1 illustrates a robotic surgery system 1000. The robotic surgery system 1000 includes a workstation 102 and an instrument station or a patient cart 104. The patient cart 104 includes a boom arm assembly 200, elevating linkage assembly 300 and control unit assembly 400. At least one tool is mountable on the moveable instrument mount, control unit or drive unit 400 that houses an instrument drive (not shown) for manipulating the tool. The tool may include an insertion device 108 that can support at least one surgical instrument (hereinafter to be interchangeably used with an "instrument" or "surgical tool") and a camera (not shown) that images a surgical site. The workstation 102 may also include a tool such as an instrument clutch (that may optionally be implemented by a foot pedal described below). The insertion device 108 can optionally support two or more instruments (not shown). The camera may optionally include a primary camera and at least one secondary camera. The primary camera and the secondary camera may provide different viewing angles, perform different functions and/or produce different images. At least one of the primary camera and the secondary camera may optionally be a two-dimensional (2D) or a three-dimensional (3D) camera. FIG. 1 is merely an example of a robotic surgery system, and certain elements may be removed, other elements added, two or more elements combined, or one element can be separated into multiple elements depending on the specification and requirements of the robotic surgery system.

The workstation 102 includes an input device for use by a user (for example, a surgeon; hereinafter to be interchangeably used with an "operator") for controlling the instrument via the instrument drive to perform surgical operations on a patient. The input device may optionally be implemented using a haptic interface device available from Force Dimension, of Switzerland, for example. The input device optionally includes a right input device 132 and a left input device 112 for controlling respective right and left instruments (not shown). The right input device 132 includes a right hand controller 122 (hereinafter to be interchangeably used with a "hand grip" or "handpiece") and the left input device 112 includes a left hand controller 124. The right and left hand controllers 122 and 124 may optionally be mechanically or electrically coupled to the respective input devices 132 and 112. Alternatively, the right and left hand controllers 122 and 124 may be wirelessly coupled to the respective input devices 132 and 112 or may be wireless coupled directly to the workstation 102. In some cases, when there are two instruments at the instrument station 104, the right and left hand controllers 122 and 124 may respectively control the two instruments. In some cases, when there are more than two instruments, the right and left hand controllers 122 and 124 may be used to select two of the multiple instruments that an operator wishes to use. In some cases, when there is only one instrument, one of the right and left hand controllers 122 and 124 may be used to select the single instrument.

The input devices 132 and 112 may generate input signals representing positions of the hand controllers 122 and 124 within an input device workspace (not shown). In some cases where the input devices 132 and 112 are coupled directly and wirelessly to the workstation, they would include the necessary sensors to allow wireless control such as an accelerometer, a gyroscope and/or magnetometer. In other cases, a wireless connection of the input devices 132 and 112 to the workstation 102 may be accomplished by the use of camera systems alone or in combination with the described sensors. The afore described sensors for wireless functionality may also be placed in each handpiece to be used in conjunction with the input devices 132 and 112 to independently verify the input device data. The workstation 102 also includes a workstation processor circuit 114, which is in communication with the input devices 132 and 112 for receiving the input signals.

The workstation 102 also includes a display 120 in communication with the workstation processor circuit 114 for displaying real time images and/or other graphical depictions of a surgical site produced by the camera associated with the instrument. The workstation 102 may optionally include right and left graphical depictions (not shown) displayed on the display 120 respectively for the right and left side instruments (not shown). The graphical depictions may optionally be displayed at a peripheral region of the display 120 to prevent obscuring a live view of the surgical workspace also displayed on the display. The display 120 may further be operable to provide other visual feedback and/or instructions to the user. A second auxiliary display 123 may be utilized to display auxiliary surgical information to the user (surgeon), displaying, for example, patient medical charts and pre-operation images. In some cases, the auxiliary display 123 may be a touch display and may also be configured to display graphics representing additional inputs for controlling the workstation 102 and/or the patient cart 104. The workstation 102 further includes a footswitch or foot pedal 126, which is actuatable by the user to provide input signals to the workstation processor circuit 114. In one case, the signal provided to the workstation processor circuit 114 may inhibit movement of the instrument while the footswitch 126 is depressed.

The patient cart 104 includes an instrument processor circuit 118 for controlling the central unit 400, insertion device 108, one or more instruments and/or one or more cameras. In such case, the instrument processor circuit 118 is in communication with the workstation processor circuit 114 via an interface cable 116 for transmitting signals between the workstation processor circuit 114 and the instrument processor circuit 118. In some cases, communication between the workstation processor circuit 114 and the processor circuit 118 may be wireless or via a computer network, and the workstation 102 may even be located remotely from the patient cart 104. Input signals are generated by the right and left input devices 132 and 112 in response to movement of the hand controllers 122 and 124 by the user within the input device workspace and the instrument is spatially positioned in a surgical workspace in response to the input signals.

Additional details of the robotic surgery system 1000 are described in U.S. patent application Ser. No. 16/174,646 filed on Oct. 30, 2018, the entirety of which is hereby incorporated by references and should be considered a part of this specification.

Boom Assembly

FIGS. 2-7 illustrates a boom arm assembly 200 of the robotic surgery system 100. The boom arm assembly 200 can include a boom assembly BA and an elevational linkage assembly 300 and couple to the control unit assembly 400.

Figure 2:
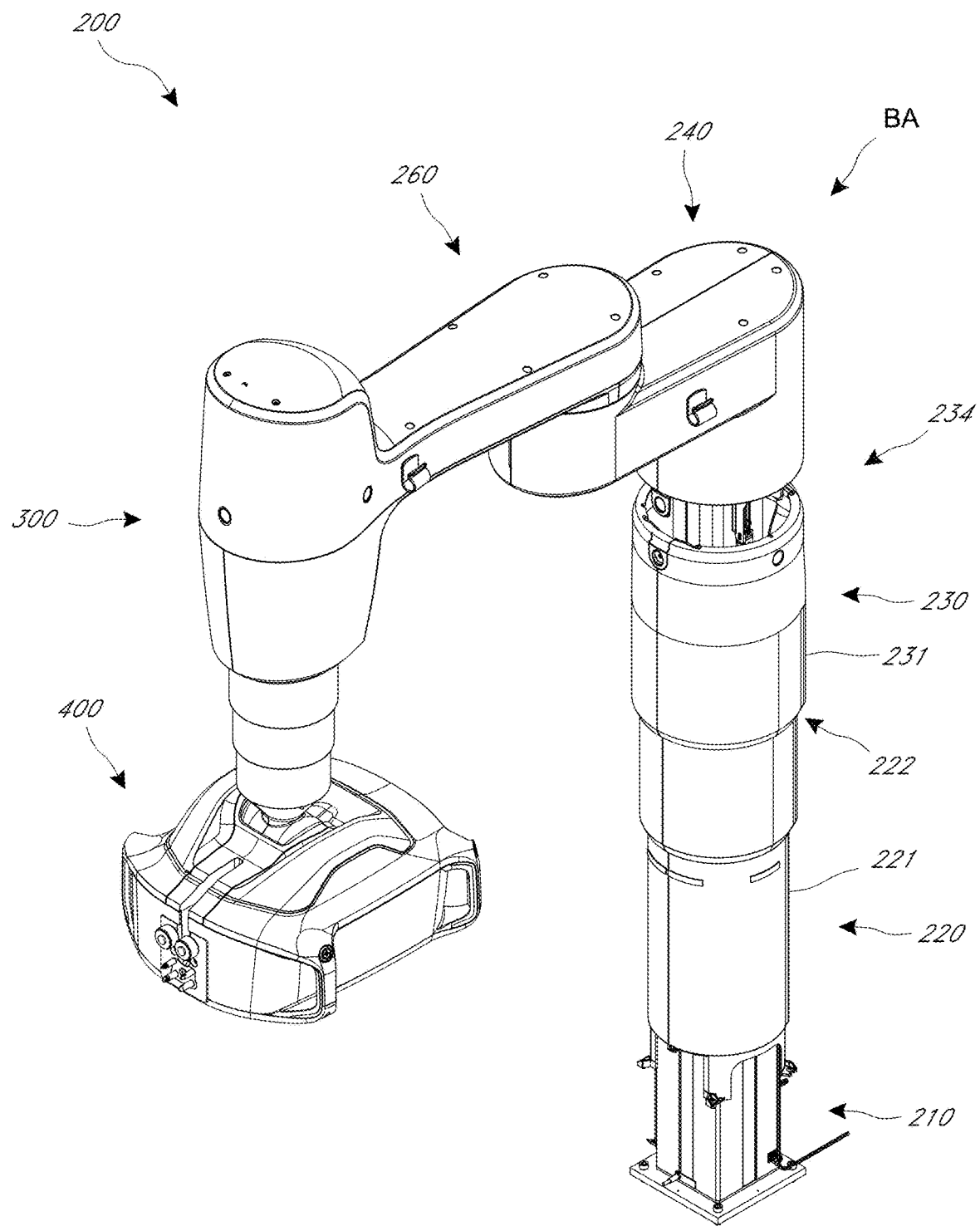
FIG. 2 is a front perspective view of a boom arm assembly and control unit assembly of the robotic surgical system.
Figure 3:
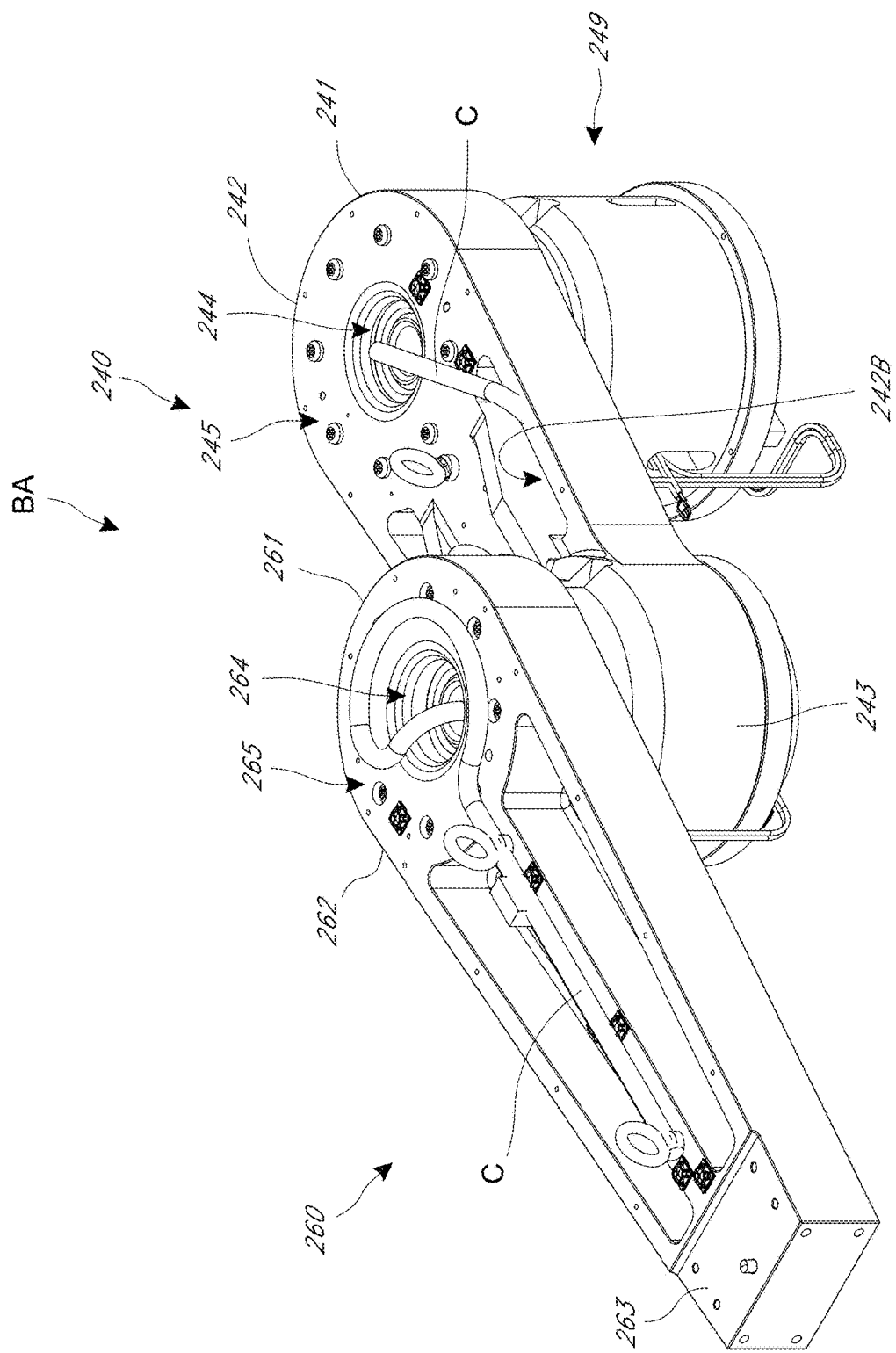
FIG. 3 is a perspective assembled view of a portion of the boom assembly.

With reference to FIG. 2, the boom arm assembly 200 includes a support base 210, a lower pillar 220 attached to the support base 210 and an upper pillar 230 movably coupled to the lower pillar 220. In one implementation, the upper pillar 230 can telescopingly extend relative to the lower pillar 220. Optionally, the upper pillar 230 can have a circular cross-section and extend within an inner perimeter of the lower pillar 220 that has a circular cross-section. Optionally, the upper pillar 230 can have an outer diameter 231 that is smaller than the outer diameter 221 of the lower pillar 220. The outer diameter 231 is optionally smaller than an inner diameter 222 of the lower pillar 220, such that the lower pillar 220 overlaps at least a portion of the upper pillar 230. Optionally, the upper pillar 230 has a measurement scale to identify the height of the boom arm assembly 200 (e.g., relative to a support base under the patient cart 104). In another implementation, the upper pillar 230 has an outer diameter 231 that is larger than the outer diameter 221 of the lower pillar 220. In another implementation, the outer diameter 221 of the lower pillar 220 is optionally smaller than an inner diameter 222 of the upper pillar 230. The support base 210 can be mounted or coupled to, disposed in or otherwise supported on or in the patient cart 104.

In one implementation, the upper pillar 230 can be manually moved (e.g., extended upward, moved downward) relative to the lower pillar 220. For example, as further described below, an operator (e.g., surgical assistant) can move the upper pillar 230 up or down relative to the lower pillar with their hands (e.g., by pressing on actuator buttons, such as on the control unit assembly 400). In particular, movement of the upper pillar 230 relative to the lower pillar 220 is not effected by a motor (e.g., electric motor). In another implementation, movement of the upper pillar 230 relative to the lower pillar 220 can be effected by a motor (e.g., by an electric motor).

With continued reference to FIG. 2, the boom arm assembly 200 includes a boom assembly BA with a proximal boom arm 240 and a distal boom arm 260. The proximal boom arm 240 is movably coupled to an upper portion 234 of the upper pillar 230, and the distal boom arm 260 is movably coupled to the proximal boom arm 240 at one end and coupled to the elevating linkage assembly 300 at its other end.

Figure 5:
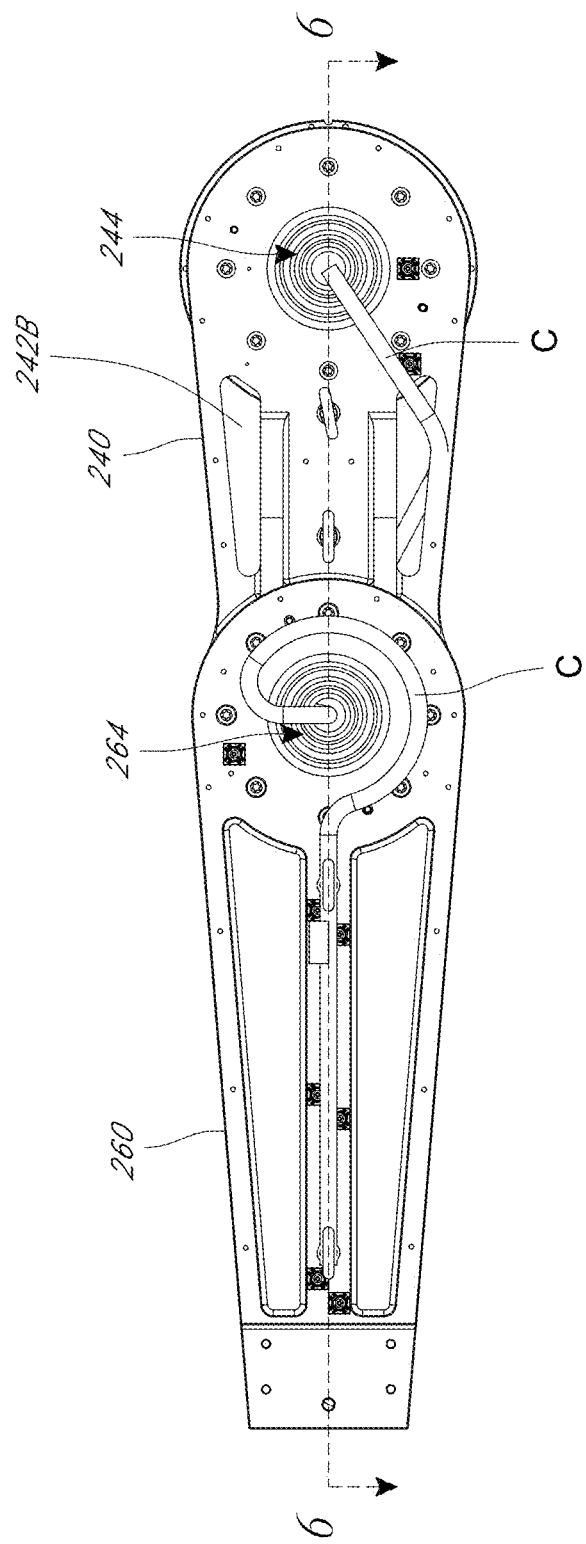
FIG. 5 is a top view of a portion of the boom assembly of FIG. 3.
Figure 6:
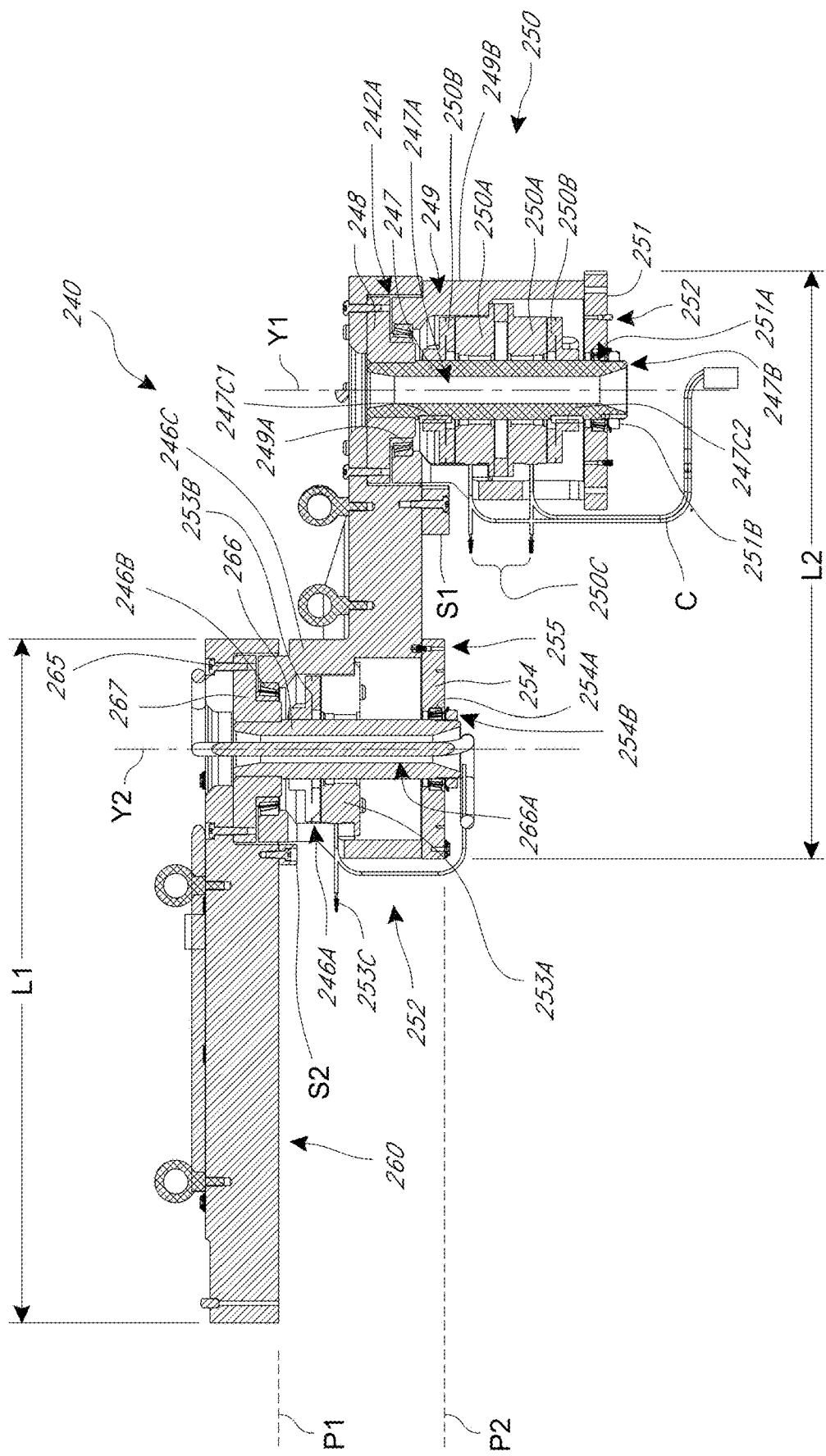
FIG. 6 is a cross-sectional side view of the boom assembly of FIG. 3.
Figure 7:
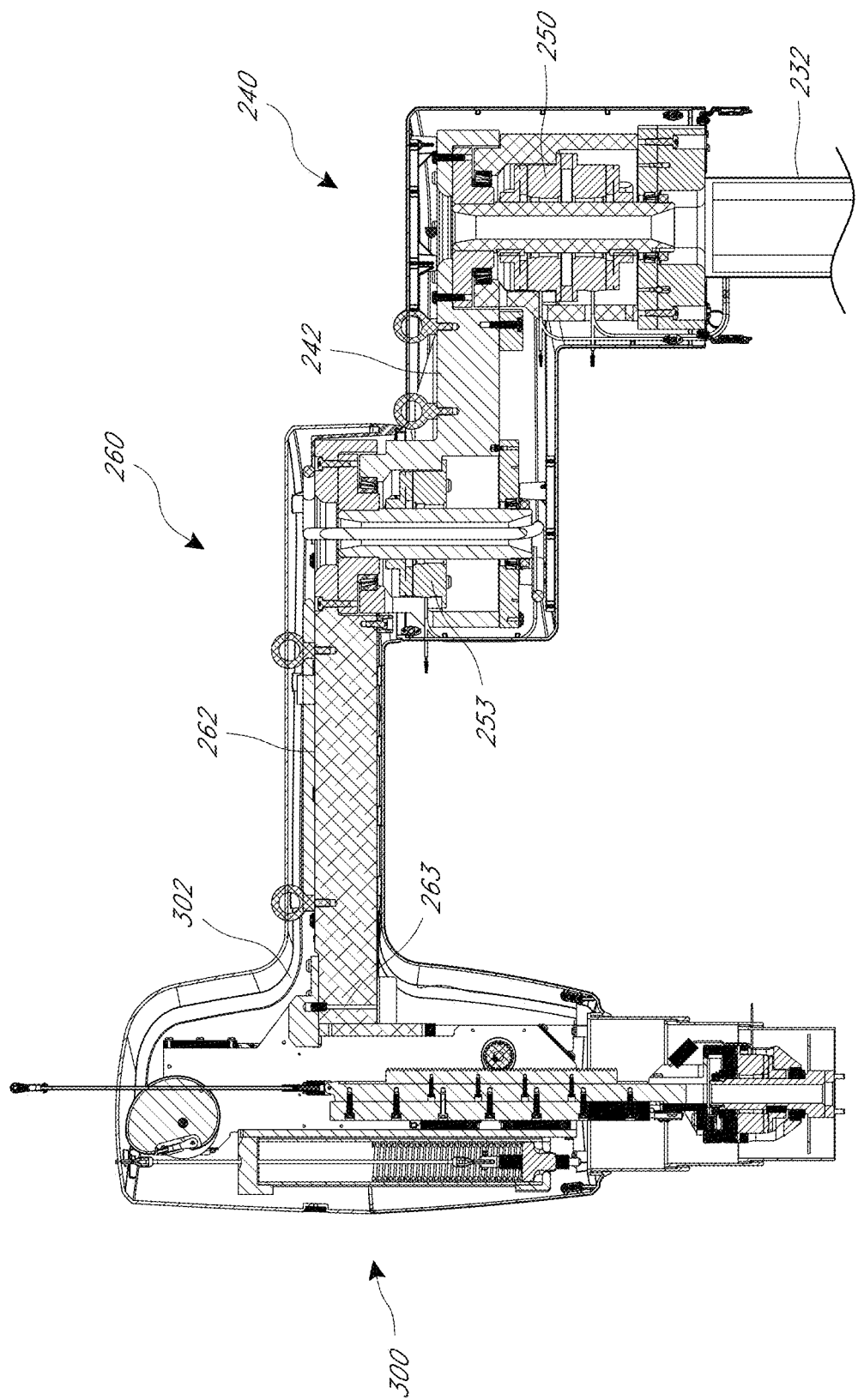
FIG. 7 is a cross-sectional side view of the boom arm assembly including the boom assembly of FIG. 3 and an elevating linkage assembly.

FIGS. 3-6 show the boom assembly BA, and FIG. 7 shows the boom assembly BA coupled to the elevating linkage assembly 300. The proximal boom arm 240 has a boom arm body 242 that extends between a proximal end 241 and a distal end 243. The proximal end 241 of the boom arm body 242 has a recess 242A that optionally receives at least a portion of a brake housing 249 (e.g., a proximal brake housing). The brake housing 249 can optionally couple to and/or be disposed in the upper portion 234 of the upper pillar 230.

Figure 4:
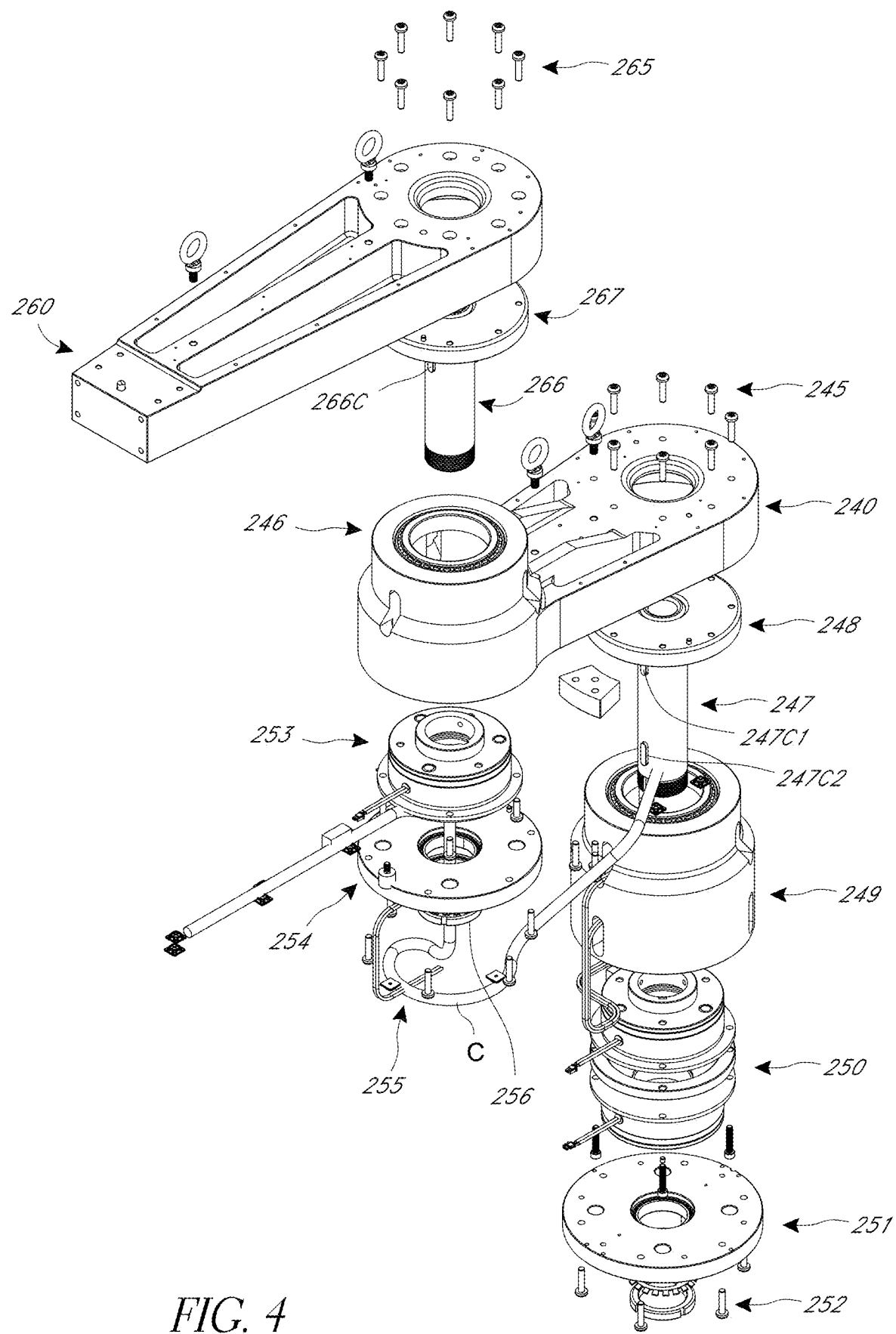
FIG. 4 is perspective exploded view of the boom assembly in FIG. 3.

With reference to FIGS. 4 and 6, the boom assembly BA can include a proximal shaft 247 with a flange 248 attached to an end of the shaft 247. The flange 248 can extend into the recess 242A of the boom arm body 242 and be coupled or attached to the boom arm body 242 by one or more fasteners (e.g., bolts) 245. The proximal shaft 247 can have a bore or opening 247A that extends along an axis Y. Optionally, the bore 247A is coaxial with an opening 244 of the boom arm body 242 when the flange 248 is disposed in the recess 242A and attached to the boom arm body 242. The shaft 247 extends through the brake housing 249 so that the flange 248 is interposed between at least a portion of the brake housing 249 and at least a portion of the boom arm body 242. A distal end of the shaft 247 extends through a base plate 251 attached to the brake housing 249 with one or more fasteners (e.g., screws, bolts) 252.

The brake housing 249 houses one or more electromagnetic brakes 250. As shown in FIGS. 4 and 6, in one implementation, the brake housing 249 houses a pair of electromagnetic brakes 250 (e.g., a double-stack permanent electromagnet brakes) actuatable via electrical connections 250C, as discussed further below. Advantageously, the use of the pair of electromagnetic brakes 250 allows the diameter of the brakes 250 (and therefore the diameter of the housing 249) to be smaller, as well as to account for the longer lever arm of the boom assembly BA from the location of the brakes 250 (e.g., to provide sufficient torque to brake the boom assembly BA). In another implementation, the one or more electromagnetic brakes 250 can be a single electromagnetic brake. In still another implementation, the one or more electromagnetic brakes 250 can be replaced with an electric motor actuatable to move and/or lock the proximal boom arm body 242 relative to the patient cart 104 (e.g., relative to the upper pillar 230).

The proximal shaft 247 extends through the electromagnetic brake(s) 250. The electromagnetic brake(s) 250 have a stator 250A and a rotor 250B. The proximal shaft 247 is coupled to the rotor 250B, so as to move together. In one implementation, the proximal shaft 247 is keyed to the rotor 250B via one or more splines 247C1, 247C2 that extend into slots in the rotor(s) 250B. With reference to FIG. 6, the brake housing 249 can include one or more bearings 249A (e.g., tapered bearings) disposed about at least a portion of the flange 248 to allow the flange 248 to rotate (along with the boom arm body 242 and proximal shaft 247) relative to the brake housing 249. Additionally, the base plate 251 can include one or more bearings 251A (e.g., tapered bearings) disposed about at least a portion of the proximal shaft 247 to allow the proximal shaft 247 to rotate relative to the base plate 251.

A locking ring 251B can be attached (e.g., threadably coupled) to a distal end 247B of the proximal shaft 247, so that the base plate 251 is interposed between the locking ring 251B and the housing 249. The proximal shaft 247 allows the proximal boom arm body 242 to rotate relative to the patient cart 104 (e.g., relative to the upper pillar 230) when the brake(s) 250 are unlocked (e.g., when the electromagnetic brake is turned off). When the brake(s) 250 are locked (e.g., when the electromagnetic brake is turned on), the proximal shaft 247 (and attached flange 248 and proximal boom arm body 242) is inhibited (e.g., prevented) from rotating relative to the patient cart 104 (e.g., relative to the upper pillar 230), thereby substantially fixing the position in space (e.g., orientation) of the proximal boom arm body 242 relative to the patient cart 104 (e.g., relative to the upper pillar 230).

With reference to FIGS. 3-6, the proximal boom arm body 242 has a hub 246 at or near the distal 243 of the boom arm body 242. The hub 246 can have a recessed portion 246A sized to receive at least a portion of an electromagnetic brake 253 therein, the electromagnetic brake 253 actuatable via electrical contact(s) 253C, as further described below. A base plate 254 can be attached to the hub 246 by one or more fasteners (e.g., screws, bolts) 255 to enclose the electromagnetic brake 253 in the hub 246.

The distal boom arm 260 can have a boom arm body 262 and extend between a proximal end 261 and a distal end 263. The boom arm body 262 can have a recessed portion 262A and an opening 264 in the proximal end 261. The boom assembly BA can include a distal shaft 266 with a flange 267 attached to an end of the shaft 266. The flange 267 can extend into the recess 262A of the boom arm body 262 and be coupled or attached to the boom arm body 262 by one or more fasteners (e.g., bolts) 265. The distal shaft 266 can have a bore or opening 266A that extends along an axis Y2. Optionally, the bore 266A is coaxial with an opening 264 of the boom arm body 262 when the flange 267 is disposed in the recess 262A and attached to the boom arm body 262. The shaft 266 extends through the hub 246 so that the flange 267 is interposed between at least a portion of the hub 246 and at least a portion of the boom arm body 262. A distal end of the shaft 266 extends through the base plate 254 attached to the hub 246.

With continued reference to FIGS. 4-6, the distal shaft 266 extends through the electromagnetic brake 253. The electromagnetic brake 253 have a stator 253A and a rotor 253B. The distal shaft 266 is coupled to the rotor 253B, so as to move together. In one implementation, the proximal shaft 266 is keyed to the rotor 253B via one or more splines 266C that extend into one or more slots in the rotor 253B. The hub 246 can include one or more bearings 246B (e.g., tapered bearings) disposed about at least a portion of the flange 267 to allow the flange 267 to rotate (along with the boom arm body 262) relative to the hub 246 (and the proximal boom arm 240). Additionally, the base plate 254 can include one or more bearings 254A (e.g., tapered bearings) disposed about at least a portion of the distal shaft 266 to allow the distal shaft 266 to rotate relative to the base plate 254.

A locking ring 254B can be attached (e.g., threadably coupled) to a distal end 266B of the distal shaft 266, so that the base plate 254 is interposed between the locking ring 254B and the hub 246. The distal shaft 266 allows the distal boom arm body 262 to rotate relative to the proximal boom arm body 242 when the brake 253 is unlocked (e.g., when the electromagnetic brake is turned off). When the brake 253 is locked (e.g., when the electromagnetic brake is turned on), the distal shaft 266 (and attached flange 267 and distal boom arm body 262) is inhibited (e.g., prevented) from rotating relative to the proximal boom arm body 242, thereby substantially fixing the position in space (e.g., orientation) of the distal boom arm body 262 relative to the proximal boom arm body 242. In another implementation, the electromagnetic brake 253 can be replaced with an electric motor actuatable to move and/or lock the distal boom arm body 262 relative to the proximal boom arm body 242.

As shown in FIG. 6, the distal boom arm 260 extends along a plane P1 generally parallel to a plane P2 along which the proximal boom arm 240 extends, with the distal boom arm 260 disposed above the proximal boom arm 240 (e.g., vertically above, relative to a support surface S under the patient cart 104). Additionally, in one implementation the distal boom arm 260 has a length L1 that is longer than a length L2 of the proximal boom arm 240, advantageously allowing the distal boom arm 260 to be rotated so that the distal boom arm 260 extends over an entire length of the proximal boom arm 240 (e.g., when viewed from above the distal boom arm 260, relative to the support surface S under the patient cart 104) and so that the distal end 263 of the distal boom arm 260 protrudes proximally of the proximal end 241 of the proximal boom arm 240. This can allow the boom arm assembly 200 to be moved into a compact retracted position (e.g., for storage). In one implementation, the proximal and distal boom arm bodies 242, 262 can have fixed lengths (e.g., each of the proximal and distal boom arms 240, 260 be a single-piece or monolithic with a fixed length). In another implementation, one or both of the proximal and distal boom arm bodies 242, 262 can have an adjustable length (e.g., a first portion that telescopingly moves relative to another portion).

Optionally, rotation of the proximal boom arm body 242 relative to the housing 249 can be limited (e.g., to less than 360 degrees); for example, as best shown in FIG. 6, a stop S1 attached to the proximal boom arm body 242 can engage (e.g., contact) at least a portion of the housing 249 to inhibit (e.g., prevent) further rotation of the proximal boom arm body 242 relative to the housing 249. Similarly, rotation of the distal boom arm body 262 relative to the proximal boom arm body 242 can optionally be limited (e.g., to less than 360 degrees); for example, as best shown in FIG. 6, a stop S2 attached to the distal boom arm body 262 can engage (e.g., contact) at least a portion of the hub 246 to inhibit (e.g., prevent) further rotation of the distal boom arm body 262 relative to the proximal boom arm body 242. In one implementation, the proximal boom arm body 242 can rotate about the housing 249 over an angular range of about 350 degrees, in one example an angular range of about 310 degrees (e.g. ±155 degrees). In one implementation, the distal boom arm body 262 can rotate about the hub 246 over an angular range of about 350 degrees, in one example an angular range of about 330 degrees (e.g., ±165 degrees).

In another implementation, the distal boom arm 260 extends along a parallel plane relative to the proximal boom arm 240, with the distal boom arm 260 disposed below the proximal boom arm 240 (e.g., vertically below, relative to a support surface S under the patient cart 104). In another implementation, the proximal boom arm 240 can be longer than the distal boom arm 260, and the distal boom arm 260 be rotatable so that proximal boom arm 240 extends over at least a portion of the length of the distal boom arm 260 (e.g., when viewed from above the proximal boom arm 240, relative to the support surface S under the patient cart 104), to allow the boom arm assembly 200 to be moved into a compact retracted position (e.g., for storage).

Advantageously, the electromagnetic brake 253 is actuatable to lock the distal boom arm 260 relative to the proximal boom arm 240 (e.g., in a particular angular orientation), and the electromagnetic brake(s) 250 are actuatable to lock the proximal boom arm 240 relative to the upper pillar 230. Advantageously, the electromagnetic brakes 250, 253 operate to lock when under zero power; therefore, in the event the robotic surgical system 1000 experiences a loss of power (e.g., due to a power outage), the electromagnetic brakes 250, 253 would automatically lock the orientation of the proximal and distal boom arms 240, 260. Additionally, the electromagnetic brakes 250, 253 allow for reduced (e.g., minimal, approximately zero) backlash or impact load between one or more of the proximal and distal boom arms 240, 260 and the upper pillar 230 when one or more of the brakes 250, 253 are engaged, thereby advantageously improving the accuracy in setting the orientation of the proximal and distal boom arms 240, 260.

As further described below, in one implementation the electromagnetic brakes 250, 253 can be unlocked (e.g., to allow the proximal and distal boom arms 240, 260 to move relative to each other and relative to the upper pillar 230) when one or more Deadman switches are actuated (e.g., pressed) by an operator, allowing power to be provided to the brakes 250, 253 via the electrical contacts 249A, 253C. When the one or more Deadman switches are disengaged by the operator (e.g., not pressed, not touched or otherwise not engaged by the operator), the brakes 240, 260 automatically engage (e.g., lock) to inhibit (e.g., prevent) rotation of the proximal and distal boom arms 240, 260 relative to each other and relative to the upper pillar 230 and/or patient cart 104.

Advantageously, cabling (e.g., electrical cabling, power/data cabling) C can be routed through one or more of the lower pillar 220, upper pillar 230, proximal boom arm 240, and distal boom arm 260 to thereby make the boom arm assembly 200 less obtrusive and inhibit (e.g., prevent) inadvertent entanglement of the cabling (e.g., with an operator, other devices in the operating room) during use. As illustrated in FIGS. 3-7, the cabling C can be routed through the bore 247A of the proximal shaft 247, via one or more openings 242B in the proximal boom arm body 242, through the bore 266A of the distal shaft 266 and along the distal boom arm body 262 to the elevating linkage assembly 300 and finally to the control unit assembly 400 as further discussed below. The cabling C can have sufficient slack to allow for the rotation of the proximal and distal boom arms 240, 260 relative to each other and relative to the upper pillar 130 and/or patient cart 104 without unduly tensioning of the cabling C. Advantageously, routing the cabling C through the bores 247A, 266A of the proximal and distal shafts 247, 266 (e.g., along the rotational axes of the proximal and distal boom arms 240, 260) allows the proximal and distal boom arms 240, 260 to rotate (when the brakes 250, 253 are unlocked) without causing the entanglement of the cabling C.

Elevating Linkage Assembly

Figure 8:
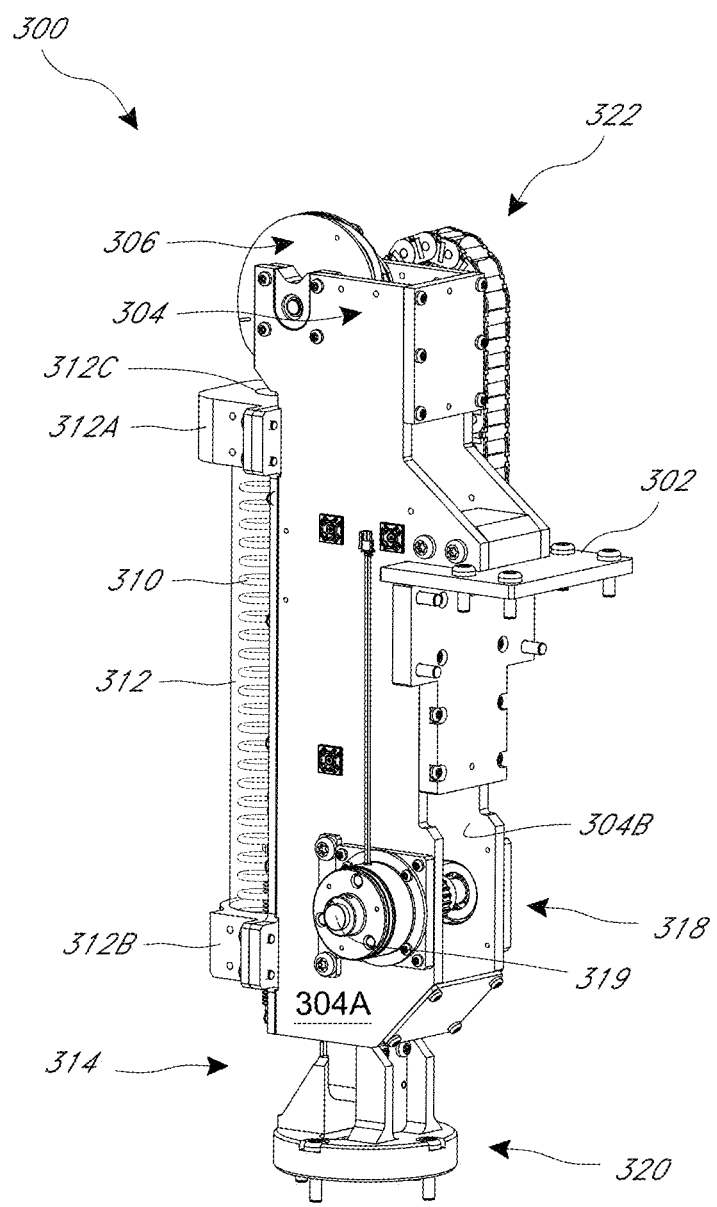
FIG. 8 is a perspective view of an elevating linkage assembly of the boom arm assembly.
Figure 9:
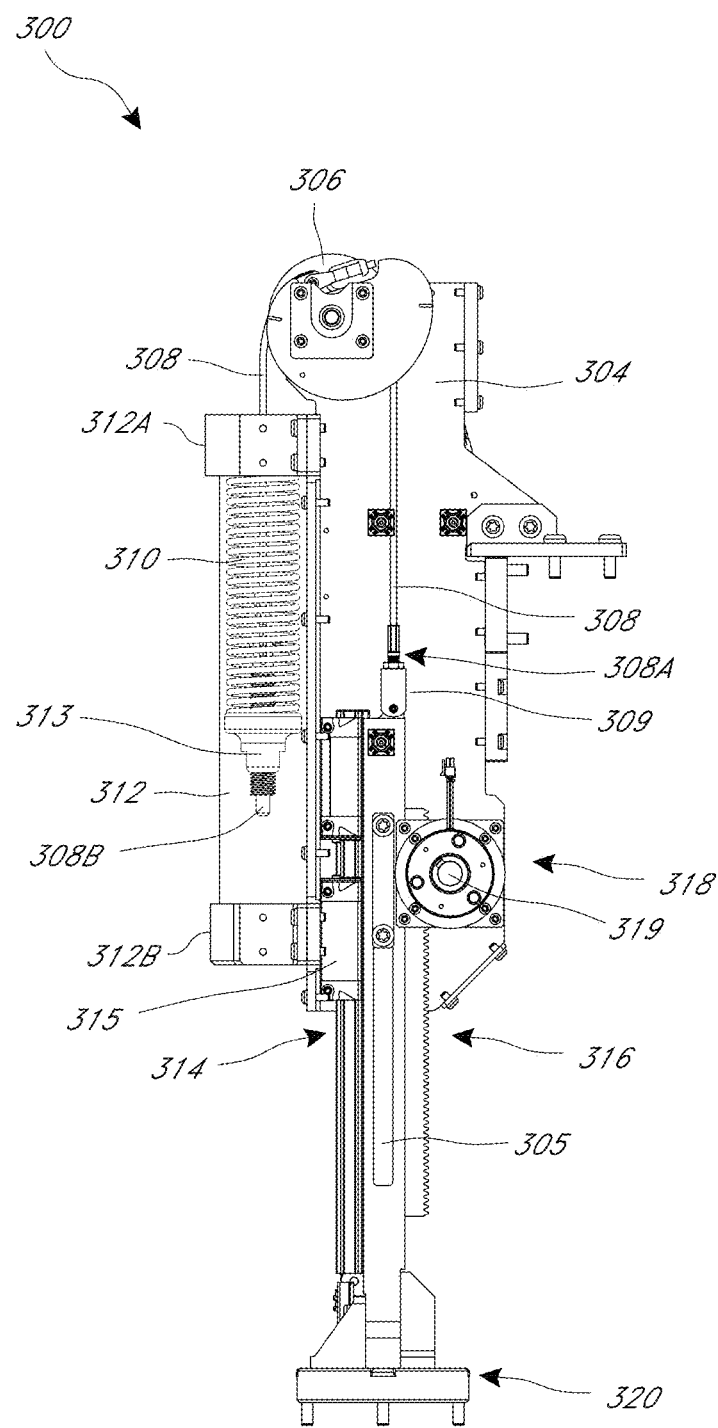
FIG. 9 is a side view of the elevating linkage assembly of FIG. 8.
Figure 10:
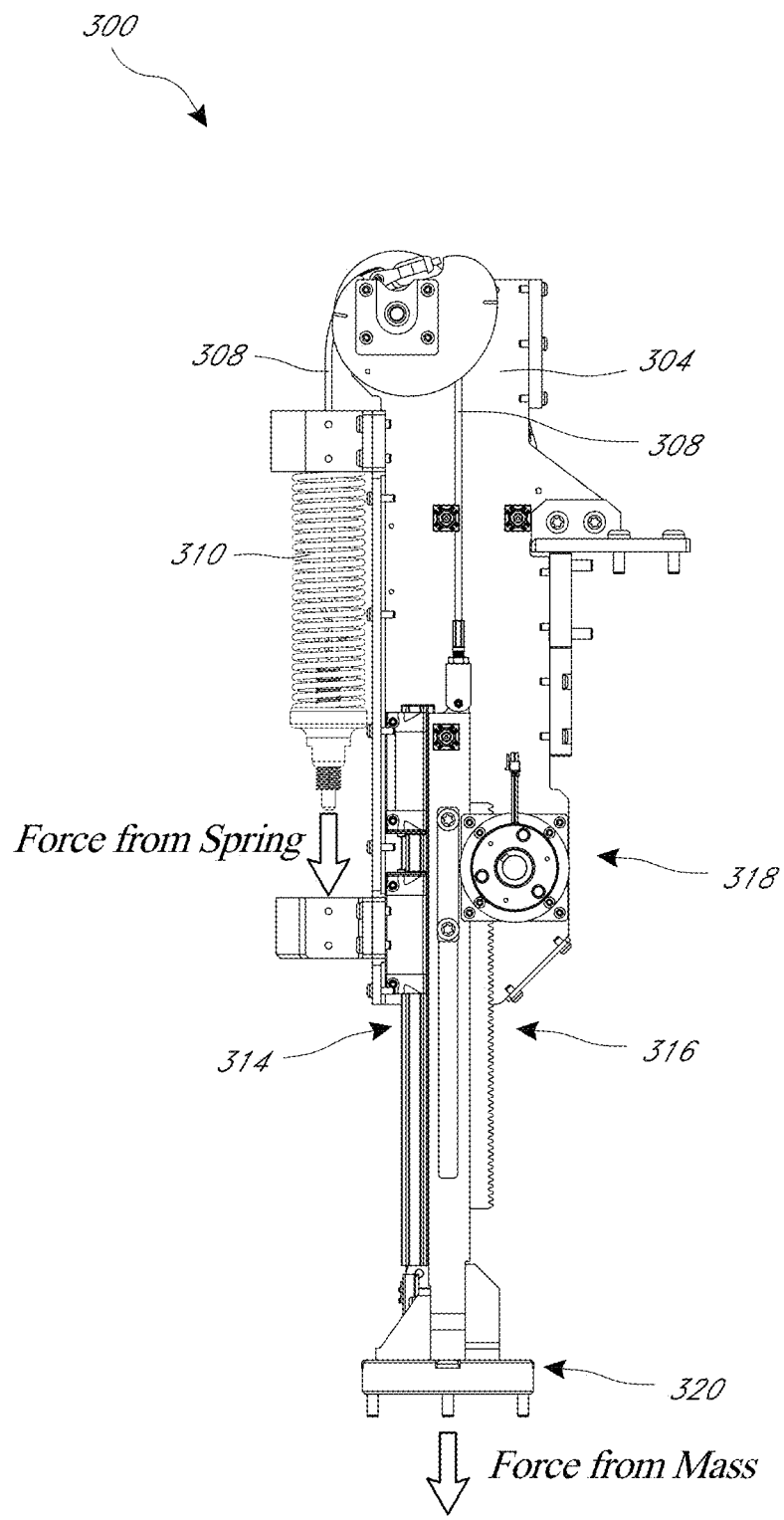
FIG. 10 is a side view of the elevating linkage assembly of FIG. 8.

FIGS. 7-13 illustrate the elevating linkage assembly 300. The elevating linkage assembly 300 has a mounting plate 302 via which it couples to the distal end 263 of the distal boom arm body 262, as shown in FIG. 7. The elevating linkage assembly 300 supports the control unit assembly 400 as shown in FIGS. 1-2 via a mounting flange 320 (e.g., with one or more bolts). Advantageously, the elevating linkage assembly 300 provides a counterbalance to the control unit assembly 400 (e.g., force from the control unit assembly 400 can be approximately the same as the force from a spring 310, as shown in FIG. 10), facilitating the vertical adjustment (e.g., manually raising and manually lowering) of the control unit assembly 400 (e.g., relative to the boom arm BA) by an operator without the operator having to support the full weight of the control unit assembly 400. In one implementation, the elevating linkage assembly 300 provides a counterbalance to the control unit assembly 400 that allows the operator to manually raise and lower the control unit assembly 400 in a weightless manner.

The elevating linkage assembly 300 has a frame 304, to which the mounting plate 302 is attached, and a cam 306 rotatably coupled to the frame 304. A support pylon 305 is movably coupled to the frame 304. The support pylon 305 couples to the mounting flange 320 that in turn couples to the control unit assembly 400. A cable 308 couples to the support pylon 305 at one end 308A of the cable 308 (e.g., via a shoulder pin 309) and wraps around at least a portion of the cam 306.

The elevating linkage assembly 300 includes a spring 310 (e.g., a compression spring, a cylindrical coil spring) enclosed in a cylinder 312 that extends between a proximal end cap 312A (e.g., that engages or contacts a proximal end of the spring 310) and a distal end cap 312B. In one implementation, the spring 310 can have a length of approximately 1 foot when in an extended state (e.g., to fit in a compact cylinder 312). However, the spring 310 can have other suitable lengths. The spring 310 can be compressed between the proximal end cap 312A of the cylinder 312 and a movable platform 313 (e.g., that can slide within the cylinder and contacts a distal end of the spring 310). The cable 208 that wraps around at least a portion of the cam 306 enters the cylinder 312 through an opening 312C in the proximal end cap 312A, extends through the spring 310 (e.g., through a central passage in the coil spring 310) and couples to the movable platform 313 at a distal end 308B of the cable 308.

The support pylon 305 can have one or more rails 314 (e.g., liner rails) on one side (e.g., attached and/or formed on one side) thereof. The rail(s) 314 can travel (e.g., slide) within corresponding runner block(s) 315 attached to the frame 304 to allow for smooth vertical actuation of the support pylon 305. The support pylon 305 can have one or more rack(s) 316 (e.g. a linear gear rack) on one side (e.g., attached and/or formed on one side) thereof. The rack(s) 316 can engage a pinion gear 317 (see FIG. 12) that is rotatably coupled to the frame 304 (e.g., via a shaft or axle 319 that extends across opposite plates 304A, 304B of the frame 304).

Figure 13:
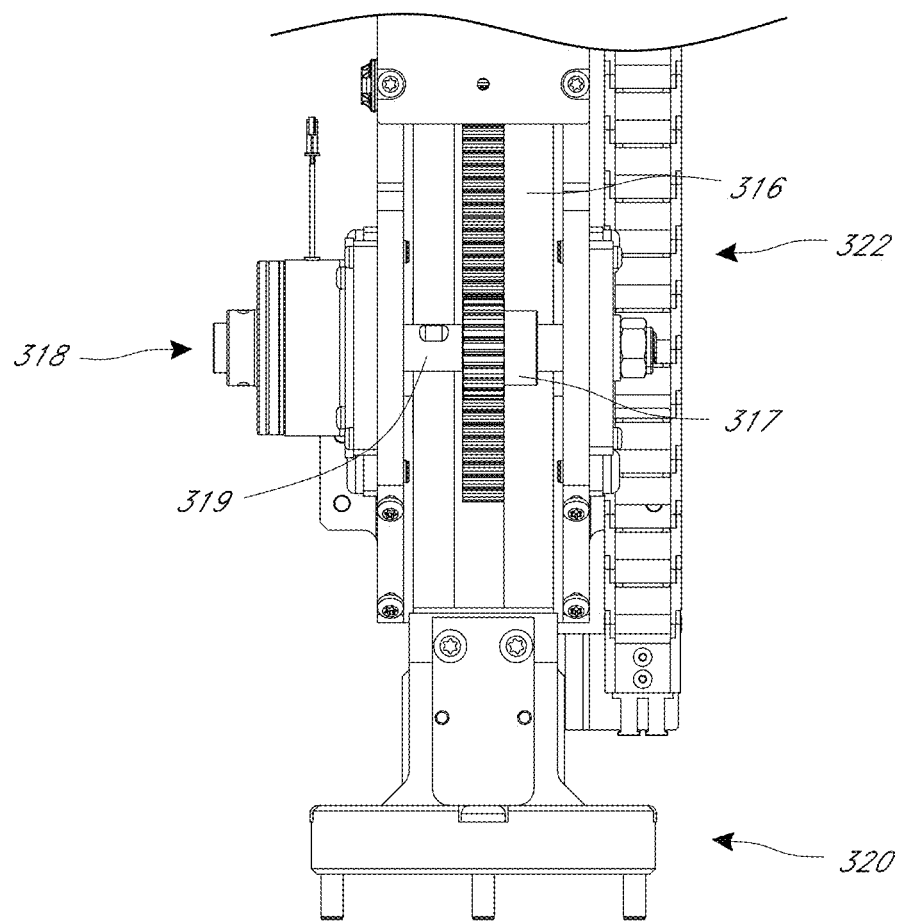
FIG. 13 is a partial rear view of the elevating linkage assembly of FIG. 8.
Figure 14:
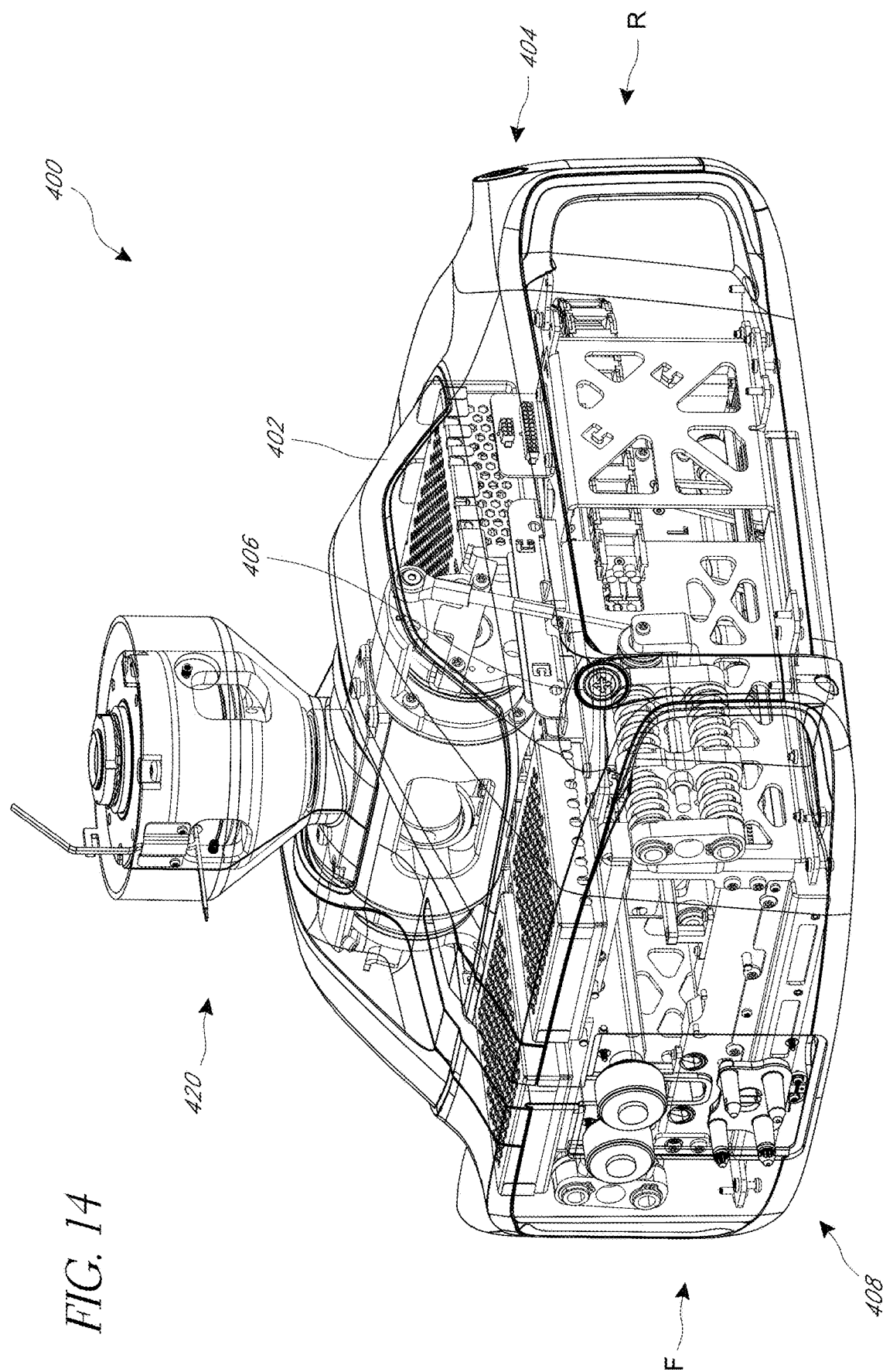
FIG. 14 is a perspective view of a control unit assembly of the robotic surgical system of FIG. 1.

The elevating linkage assembly 300 also includes a brake 318. In one implementation, the brake 318 can be an electromagnetic brake 318. The brake 318 can be coupled to the frame 304 and coupled to the axle 319 (e.g., in a keyed or spline connection). When in the unlocked position (e.g., when the electromagnet is powered) the elevating linkage assembly 300 can allow movement (e.g., vertical or axial movement) of the support pylon 305 relative to the frame 304 to thereby allow movement (e.g., raising or lowering) of the control unit assembly 400. When in the locked position (e.g. when the electromagnet is not powered or off) the elevating linkage assembly 300 can inhibit (e.g., prevent, lock) movement of the support pylon 305, thereby locking the vertical position of the control unit assembly 400. As shown in FIG. 13, the elevating linkage assembly 300 can also have a cable management member 322 (e.g., cable management tray) can engage the cable C to maintain it in an ordered manner (e.g., inhibit its tangling) as it passes from the distal boom arm body 262, through the elevating linkage assembly 300 and to the control unit assembly 400.

Figure 11B:
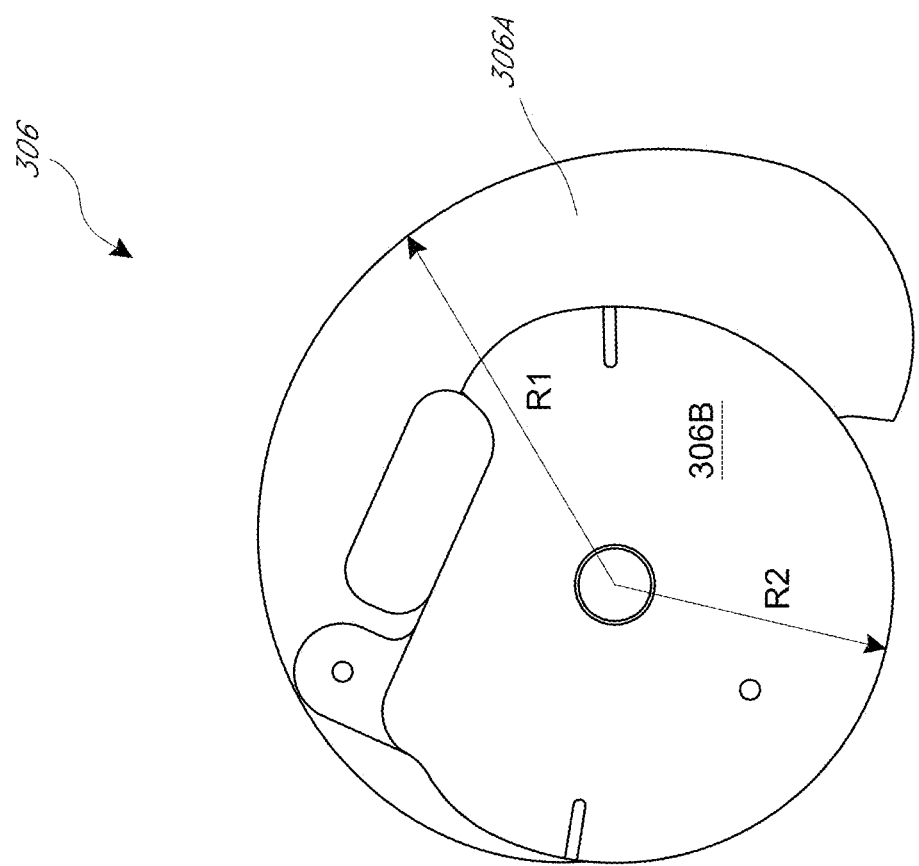
FIG. 11B is a front view of the variable cam of FIG. 11A.
Figure 11A:
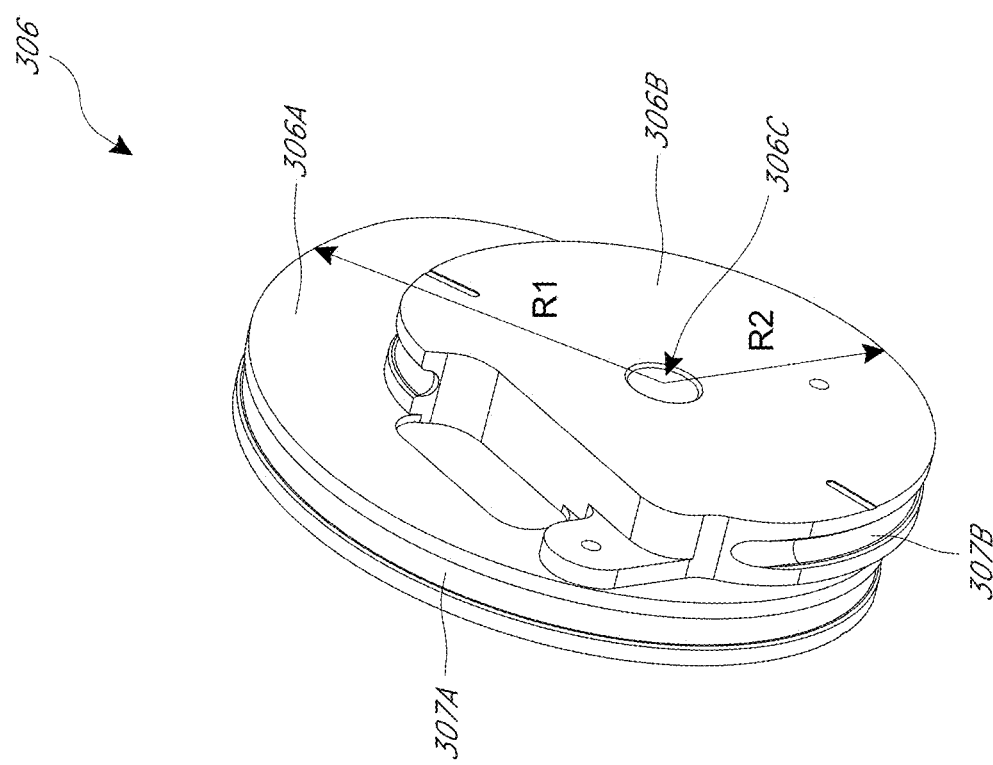
FIG. 11A is a perspective view of a variable cam of the elevating linkage assembly of FIG. 8.
Figure 12:
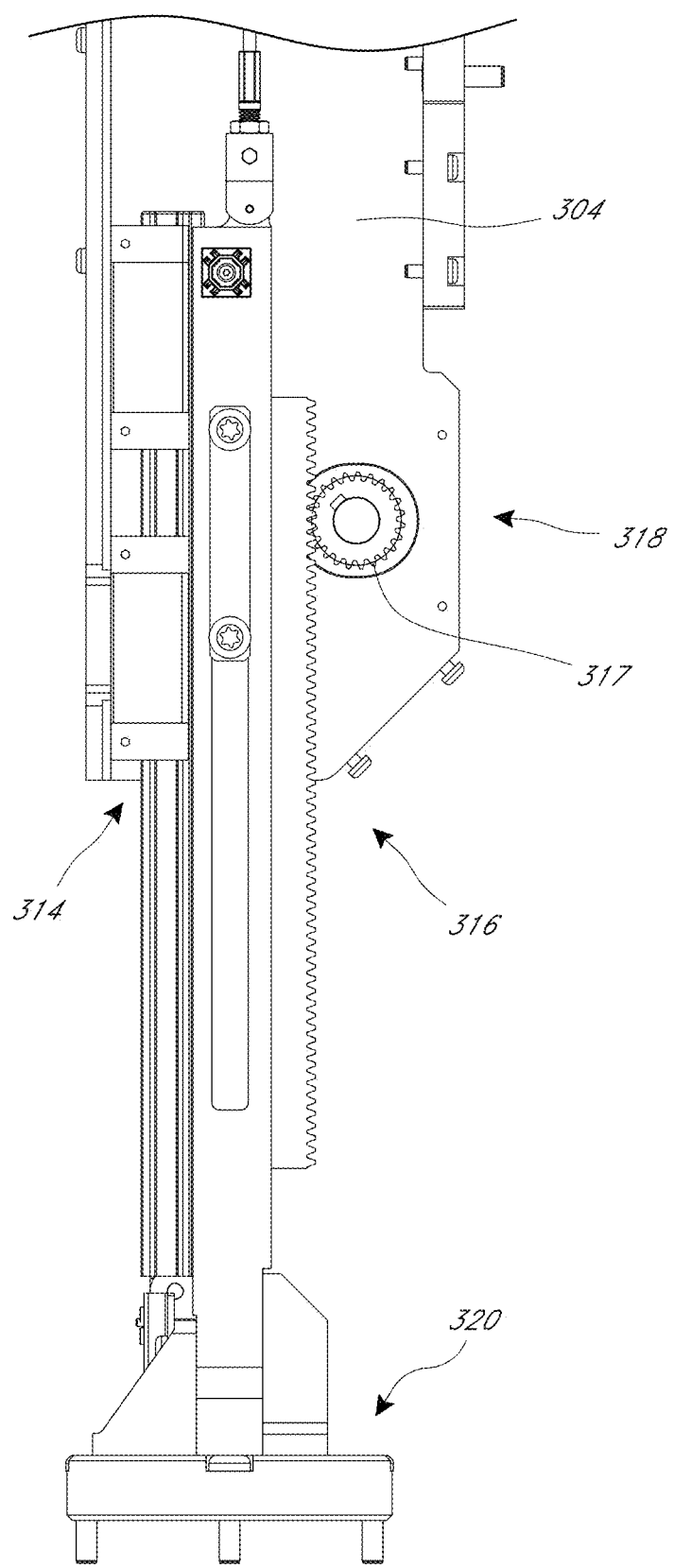
FIG. 12 is a partial side view of the elevating linkage assembly of FIG. 8.

With reference to FIGS. 11A-11B, the cam 306 can have a first cam body 306A with a variable radius R1 and a second cam body 306B with a constant radius R2 measured from a bore 306C that defines the axis of rotation of the cam 306. The cam 306 can rotatably couple to the frame 304 via an axle that extends through the bore 306C (e.g., and that couples to the opposing walls 304A, 304B of the frame 304). The first cam body 306A has a first groove 307A and the second cam body 306B has a second groove 307B. The cable 308 can extend along at least a portion of the groove 307A of the first cam body 306A with the variable radius R1. Optionally, at least a portion of the cable 308 can extend along at least a portion of the groove 307B of the second cam body 306B. In one implementation, the grooves 307A, 307B join at a transition between the first cam body 306A and the second cam body 306B.

Advantageously, the rate of change in the force of the spring 310 is substantially equal to (e.g., equal to) the rate of change in the radius R1 of the first cam body 306A. This results in a substantially equal or constant torque, which facilitates the generally weightless movement of the control unit assembly 400 during a lifting or lower motion of the elevating linkage assembly 300.

As illustrated in FIGS. 8-10, the cylinder 312 and spring 310 extend generally vertically (e.g., along an axis that is parallel to an axis of the support pylon 305). In another implementation, the cylinder 312 and spring 310 can extend generally horizontally (e.g., extend generally perpendicular to the axis of the support pylon 305). As shown in FIG. 9, the spring 310 can be disposed on a front side of the elevating linkage assembly 300. However, in other implementations the spring 310 and cylinder 312 can instead be on a side surface (or a rear surface) of the elevating linkage assembly, and the orientation of the cam 306 adjusted so that the cable 308 is fed from a surface (e.g., groove 307A) of the cam 306 into the cylinder 312.

As discussed above, the elevating linkage assembly 300 can have a brake 318 to lock and unlock the position of the support pylon 305. In another implementation, a motor (e.g., an electric motor) can additionally or alternatively be used. In one implementation, the motor can be used instead of the brake 318, where the motor actively moves the support pylon 305 via the rack 316 and pinion 317 to raise and lower the control unit assembly 400. In another implementation, the motor can supplement the brake 318 (e.g., where the cam 306 instead has a constant radius, and the motor operates to supplement the brake 318 as the force of the spring 310 changes to maintain a substantially constant torque).

Control Unit Assembly

FIGS. 14-20 illustrate certain features of the control unit assembly 400 for the robotic surgical system 1000. As discussed previously, one or more tools can be removably mounted to and operable via the control unit assembly 400. The control unit assembly 400 can extend between a rear end R and a front end F and optionally have an outer skin 402. The control unit assembly 400 also can include a connector 408 that couples to (e.g., removably couples to) the insertion device 108 through which the tools extend.

The control unit assembly 400 can have one or more user interfaces 404 proximate the rear end R and one or more user interfaces 406 proximate the front end F. In one implementation, the one or more user interfaces 404 are a pair of interfaces at the front end F, and the one or more user interfaces 406 are a pair of interfaces at the rear end R. Optionally, the interfaces 404, 406 can be located at or near corners of the control unit assembly 400 (e.g., proximate handles of the control unit assembly 400 that the operator can grab while engaging the interfaces 404, 406). In one implementation, the one or more user interfaces 404, 406 are actuatable to unlock one or more of the brakes disclosed herein to allow movement of one or more portions of the robotic surgical system 1000 (e.g., one or more portions of the boom assembly BA, elevating linkage assembly 300 and/or control unit assembly 400). In one implementation, the one or more user interfaces 404, 406 can be depressible buttons. In another implementation, the one or more user interfaces 404, 406 can be tactile sensors (e.g., capacitance sensors). In still another implementation, the one or more user interfaces 404, 406 can be movable (e.g., pivotable, slidable) levers. Further discussion of the user interfaces 404, 406 is provided below.

The control unit assembly 400 can include one or more of a chassis 410, a yaw control assembly 420, a pitch control assembly 440 and a counterbalance assembly 460. The counterbalance assembly 460 can include a pair of counterbalance assemblies 460A, 460B coupled to opposite sides of the chassis 410.

Figure 18A:
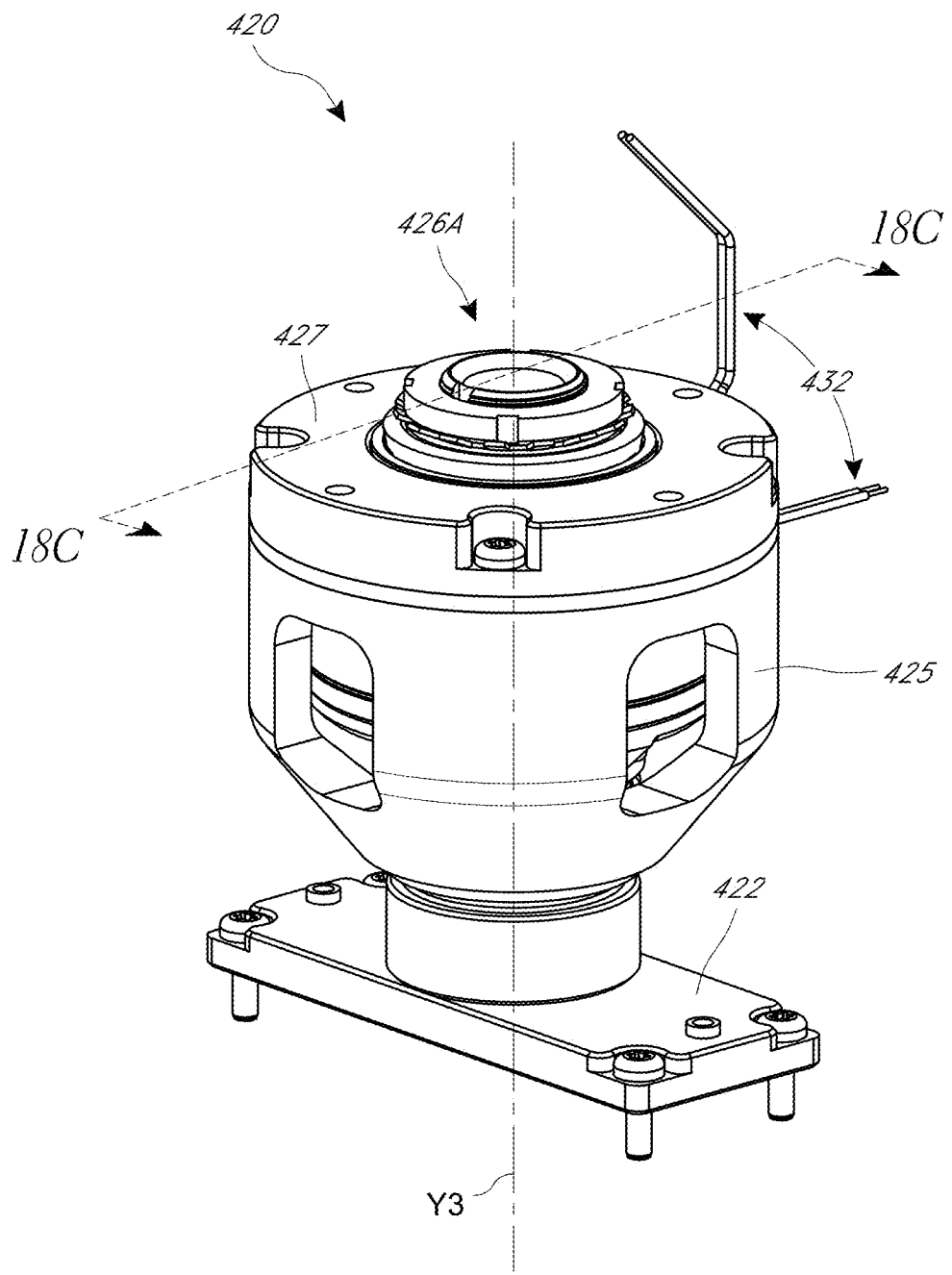
FIG. 18A is a perspective assembled view of a yaw control assembly of the control unit assembly of FIG. 15.
Figure 18B:
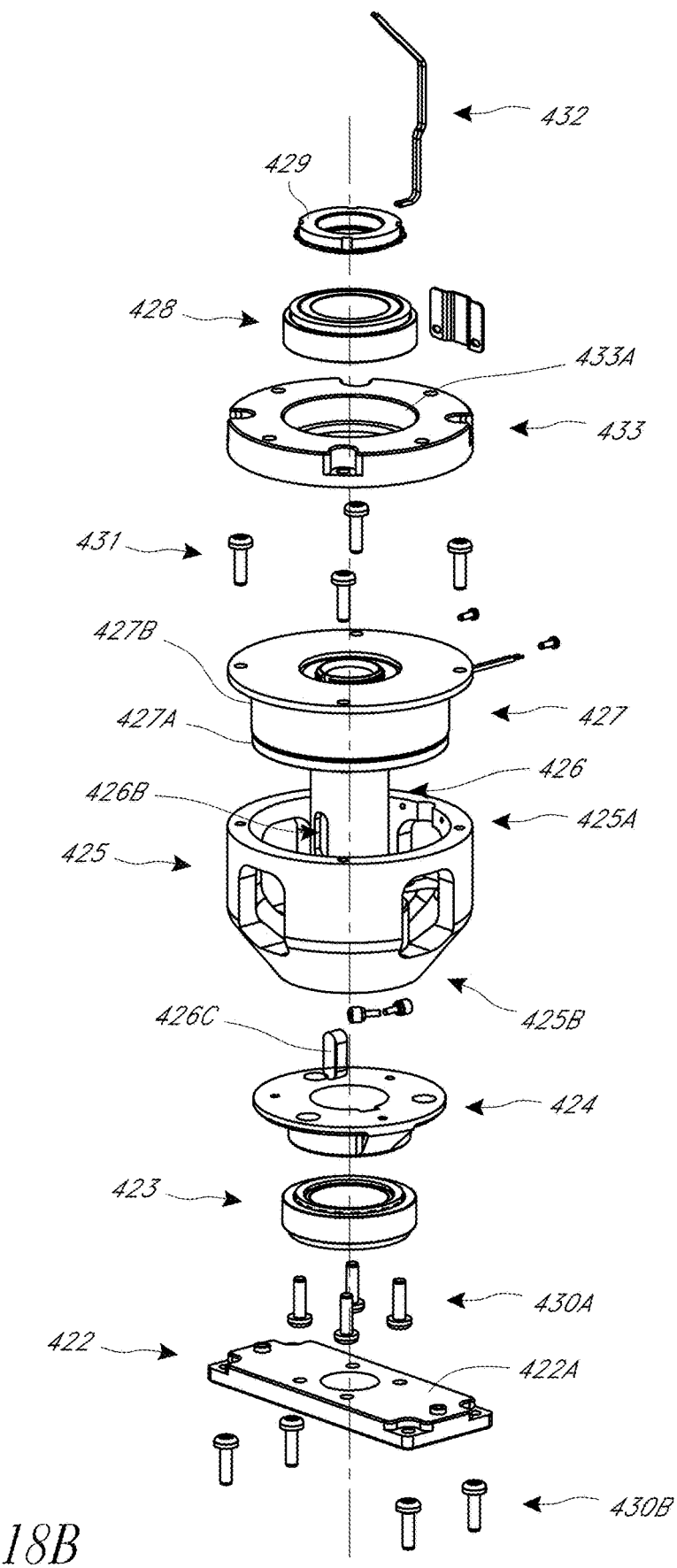
FIG. 18B is a perspective exploded view of the yaw control assembly of FIG. 18A.
Figure 18C:
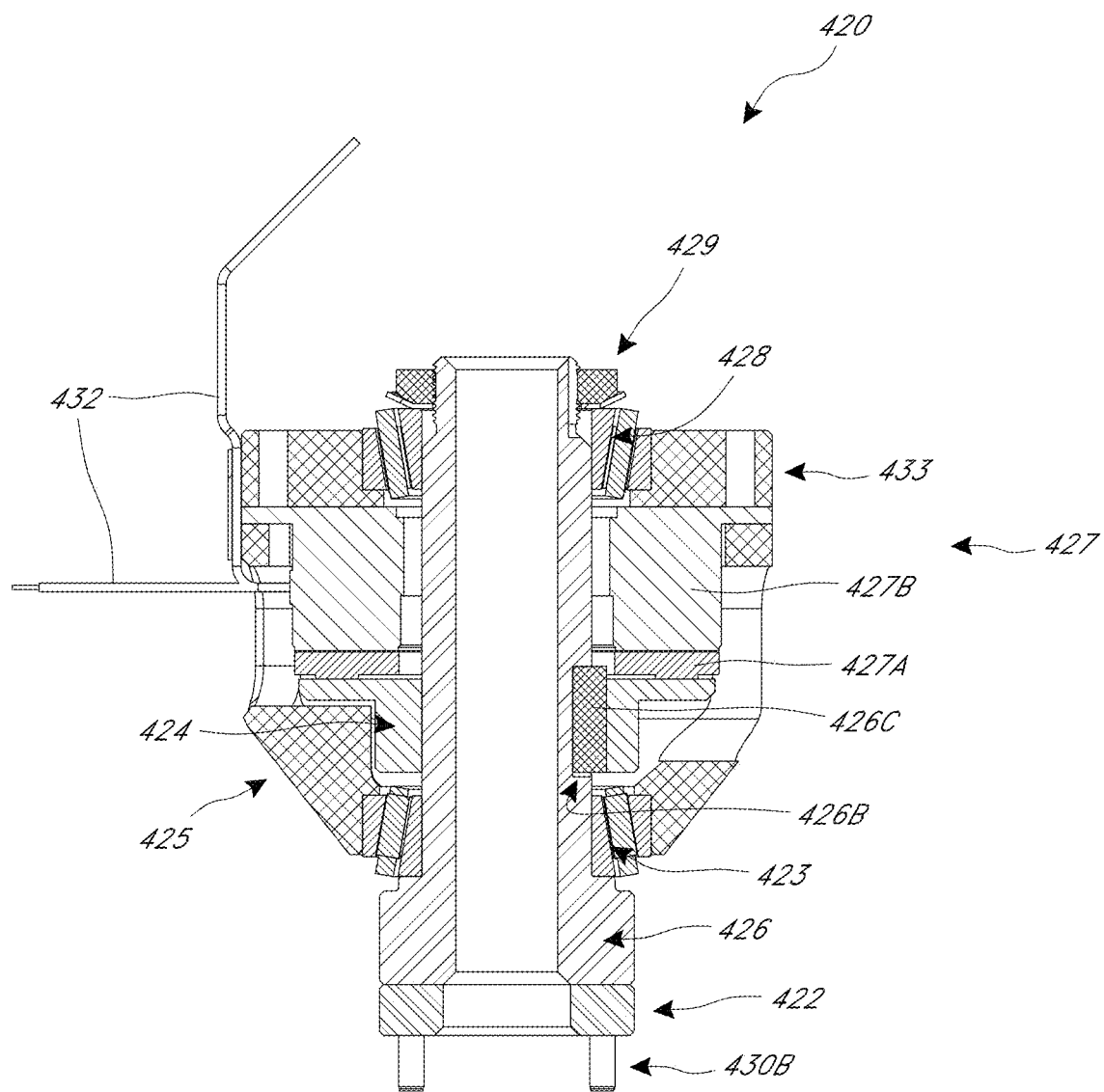
FIG. 18C is a cross-sectional view of the yaw control assembly of FIG. 18A.

With reference to FIGS. 18A-18C, the yaw control assembly 420 can optionally include a mounting plate 422. The yaw control assembly 420 can couple with the pitch control assembly 440 via one or more fasteners 430B (e.g., bolts) that fasten the mounting plate 422 to the pitch control assembly 440. A bearing 423 (e.g., tapered bearing) can sit on a surface 422A of the mounting plate 422, and a hub 424 can be disposed at least partially above the bearing 423 so that the bearing 423 is interposed between the hub 424 and the mounting plate 422. The hub 424 can couple with a housing 425 at or proximate a distal end 425A of the housing 425. Optionally, the hub 424 can at least partially extend through the housing 425 (e.g., protrude from the distal end 425A of the housing 425). The mounting plate 422 optionally couples with the hub 423 via one or more fasteners 430A (e.g., bolts).

The housing 425 can have an axle 426 that extends along the axis (e.g., central axis, axis of symmetry) of the housing 425. A brake 427 (e.g., an electromagnetic brake) can be at least partially housed in the housing 425 and disposed about the axle 426. The brake 427 can have an annular (e.g., donut) shape. A cover or top 433 can be coupled with the housing 425 at or proximate a proximal end 425A of the housing 425 with one or more fasteners 431 (e.g., bolts). The cover 433 can have an openings 433A sized to receive a bearing (e.g., a tapered bearing) 428 therein. At least a proximal portion 426A of the axle 426 can extend through the bearing 428, and a locking ring 429 can couple to the proximal portion 426A adjacent the bearing 248.

As shown in FIG. 18B-18C, the axle 426 can optionally have one or more slots 426B that can at least partially receive one or more splines 426C. The shaft 426 can be coupled to a rotor 427A via a key-slot or splined connection in the hub 424 attached to the rotor 427A, and the brake 427 can selectively brake the movement of the rotor 427A relative to a stator 427B.

In operation, when the brake 427 is unlocked (e.g., electromagnetic brake is actuated via electrical connections 432 to allow movement of one portion of the yaw control assembly 420 relative to another portion of the yaw control assembly 420), one or more of the plate 422, bearing 423, hub 424 and axle 426 can rotate or pivot relative to a rest of the yaw control assembly 420. When the brake 427 is locked (e.g., when the electromagnetic brake is turned off so that it locks in place), the brake 427 can inhibit (e.g., prevent) movement of the rotor 427A, thereby preventing rotation of one or more of the axle 426, hub 424, bearing 423 and the mounting plate 422. Accordingly, the yaw control assembly 420 can be operated to allow the adjustment (e.g., manual adjustment by an operator) of the orientation of the mounting plate 422 relative to the axis Y3 of the axle 426 (and thereby the orientation of the control unit assembly 400 disposed below the mounting plate 422) to adjust the orientation of the control unit assembly 400 in a yaw direction.

Figure 19A:
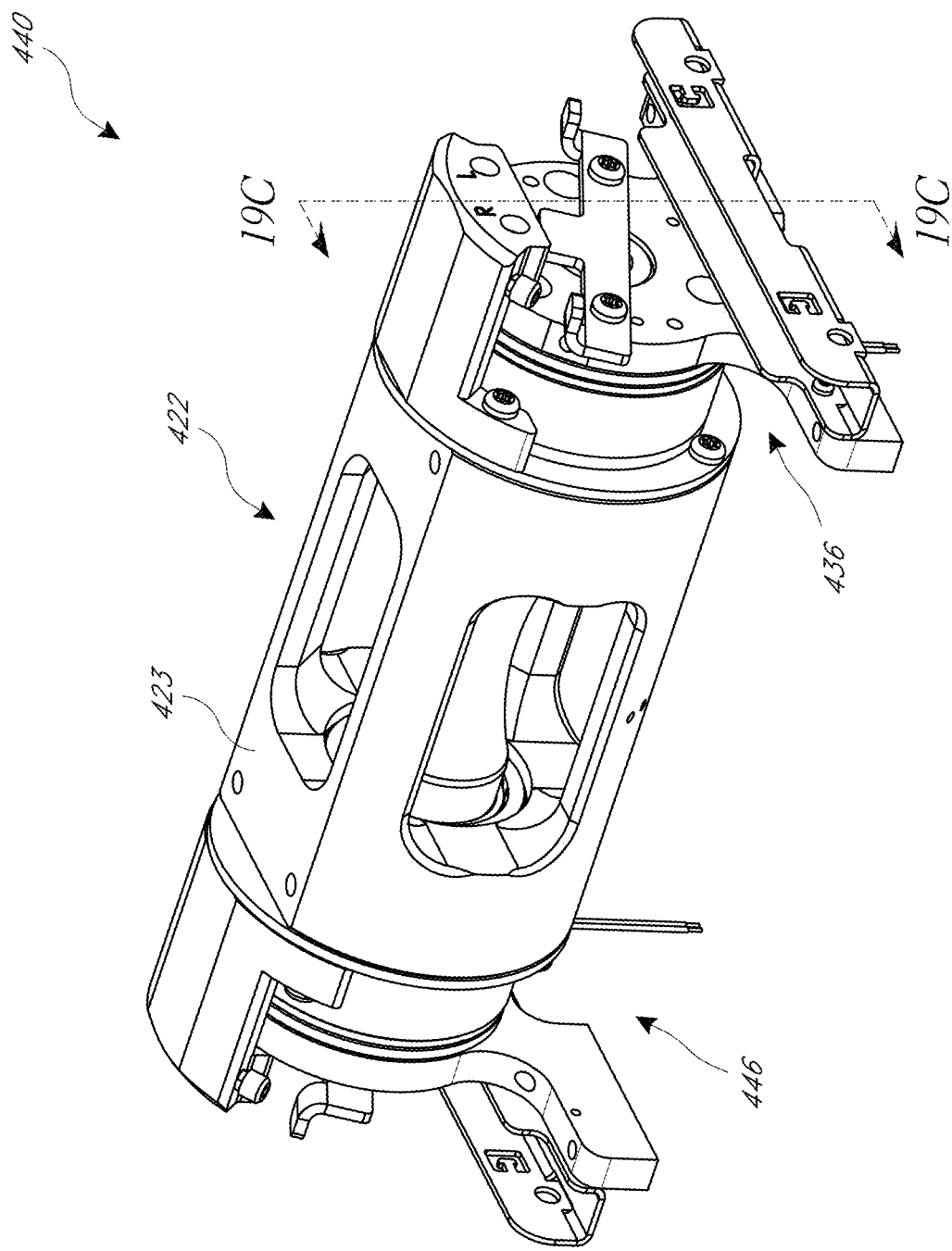
FIG. 19A is a perspective assembled view of a pitch control assembly of the control unit assembly of FIG. 15.
Figure 19B:
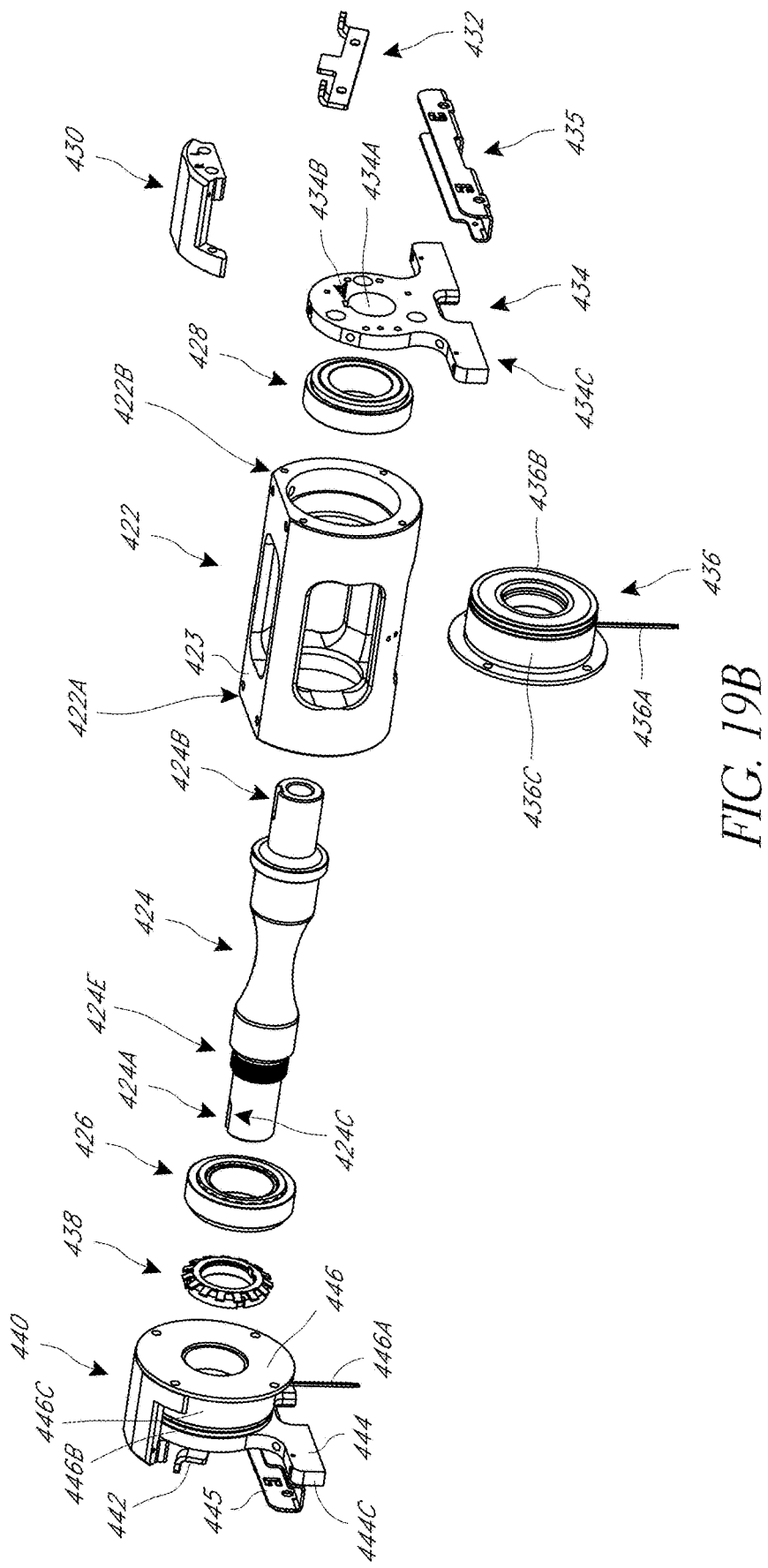
FIG. 19B is a perspective exploded view of the pitch control assembly of FIG. 19A.
Figure 19C:
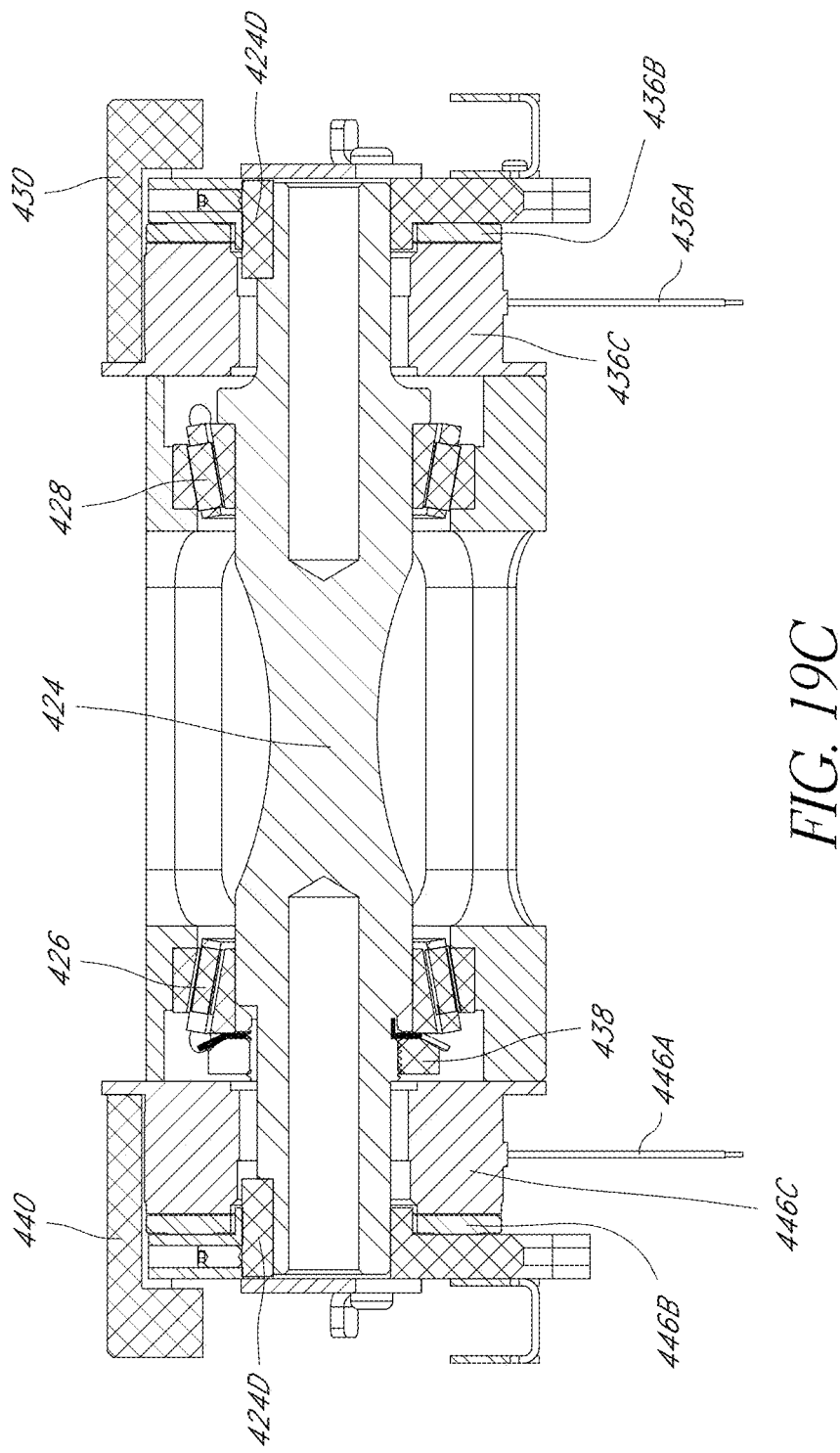
FIG. 19C is a cross-sectional view of the pitch control assembly of FIG. 19A.

With reference to FIGS. 19A-19C, the pitch control assembly 440 has a housing 422 with a surface 423 that can couple with the mounting plate 422 of the yaw control assembly 420 (e.g., via the one or more fasteners 430B). Optionally, the housing 422 can be generally cylindrical in shape. A shaft 424 can extend between a proximal end 424A and a distal end 424B, where the proximal and distal ends 424A, 424B of the shaft 424 can at least partially extend from opposite ends of the housing 422. Optionally, the shaft 424 can have one or more slots 424C at one or both ends 424A, 424B. The one or more slots 424C can have (e.g., can receive therein) a corresponding spline 424D. Optionally, a pair of bearings 426, 428 (e.g., tapered bearings) can be disposed in corresponding openings 422A, 422B at or proximate opposite ends of the housing 422 (e.g., so that the bearings 426, 428 do not protrude from the proximal and distal ends of the housing 422). The proximal and distal ends 424A, 424B of the shaft 424 can extend through the bearings 426, 428.

Optionally, a pair of brakes 436, 446 (e.g., electromagnetic brakes) can be disposed on opposite sides of the housing 422. Advantageously, the pair of brakes 436, 446 provides for increased stability and reduces a wobbling motion of the pitch control assembly 440. In another implementation, a single brake (e.g. an electromagnetic brake) can instead be used and disposed along the shaft 424.

Optionally, a locking ring 438 can be disposed adjacent the bearing 426 and couple (e.g., threadably couple) to a portion (e.g., threaded portion) 424E of the shaft 424. A pair of support brackets 430, 440 can attach (e.g., via fasteners) to opposite ends of the housing 422, at least a flange portion of the brakes 436, 446 interposed between the brackets 430, 440 and the opposite ends of the housing 422. A pair of end plates 434, 444 can be disposed adjacent the brakes 436, 446, where the brackets 430, 440 extend over at least a portion of the end plates 434, 444. The end plates 434, 444 can have openings 434A, 444A through which the distal and proximal ends 424B, 424A of the shaft 424 at least partially extend. The openings 434A, 444A can have keyed slot 434B, 444B that can receive the spline 424D on the shaft 424, thereby fixedly coupling the end plates 434, 444 to the shaft 424.

A pair of travel stop plates 432, 442 can attach to the end plates 434, 444. The travel stop plates 432, 442 can limit the rotational travel of the pitch control assembly 440 by engaging the brackets 430, 440. In one implementation, the travel stop plates 432, 442 can limit rotational travel (e.g., in pitch) from a neutral (horizontal) position to between about 10 degrees up and 50 degrees down. However, the attachment of the travel stop plates 432, 442 on the end plates 434, 444 can be adjusted to provide a different range of travel.

Figure 17:
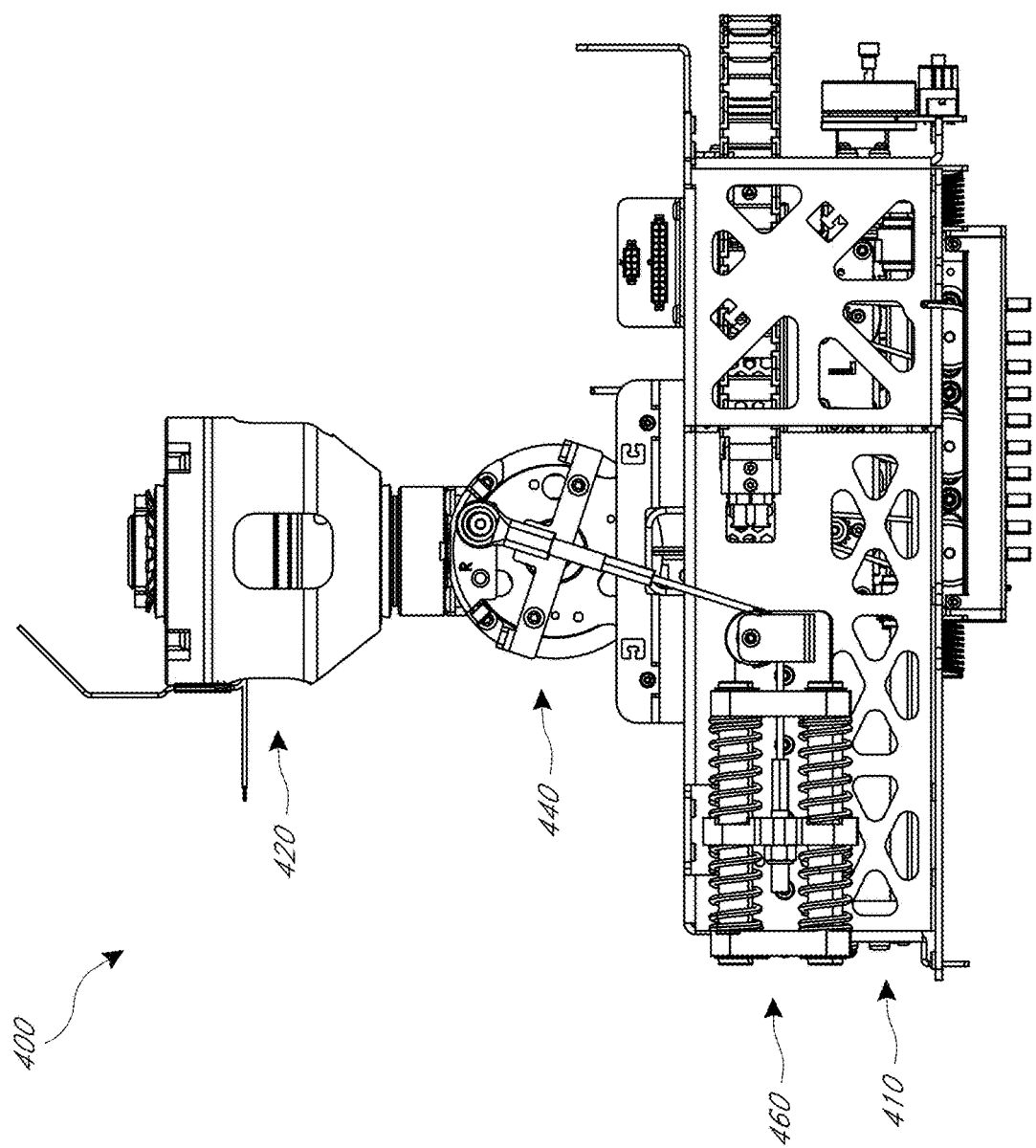
FIG. 17 is a side view of the control unit assembly of FIG. 15.

The pitch control assembly 440 can couple to the chassis 410 of the control unit assembly 400 via one or more fasteners (e.g. bolts) that couple one or more legs 434C, 444C of the end plates 434, 444 to the chassis 410. The pitch control assembly 440 can couple to the chassis 410 substantially at a center location along the length of the control unit assembly 400, as shown in FIG. 17. In operation, the end plates 434, 444 can rotate relative to the housing 422 (e.g., relative to the yaw control assembly 420 attached to the housing 422) when the brakes 436, 446 are unlocked (e.g., when the electromagnetic brakes 436, 446 are actuated via electrical connections 436A, 446A to allow rotation of one portion of the pitch control assembly 440 relative to another portion of the pitch control assembly 440). For example, when the brakes 436, 446 are unlocked, rotor(s) 436B, 446B can rotate relative to stators 436C, 446C of the brakes 436, 446. When the brakes 436, 446 are locked (e.g., when the electromagnetic brakes 436, 446 are turned off so that they locks in place), the brakes 436, 446 can inhibit (e.g., prevent) movement of the rotor(s) 436B, 446B relative to the stators 436C, 446C, thereby preventing rotation of the shaft 424 and thereby the end plates 434, 444 relative to the housing 422.

Advantageously, the yaw control assembly 420 and pitch control assembly 440 can auto lock upon a loss of power, as further discussed below. Therefore, the brake 427 in the yaw control assembly 420 and the brake(s) 436, 446 in the pitch control assembly 440 are locked when the user interfaces 404, 406 are disengaged or otherwise not engaged (and/or when there is no power, or loss of power), and unlock when the user interfaces 404, 406 are engaged (and there is power provided to the brakes). Additionally or alternatively, the pitch control assembly 440 and/or yaw control assembly 420 are operable to lock and unlock when the one or more robotic tools are in a retracted position in the control unit assembly 400, but lock (e.g., automatically lock) once the one or more robotic tools are moved into the extended position relative to the control unit assembly 400. In another implementation, one or more of the brake 427 in the yaw control assembly 420 and the brake(s) 436, 446 in the pitch control assembly 440 can instead be motor(s) (e.g., electric motors) operable to effect the yaw and/or pitch movement.

Figure 15:
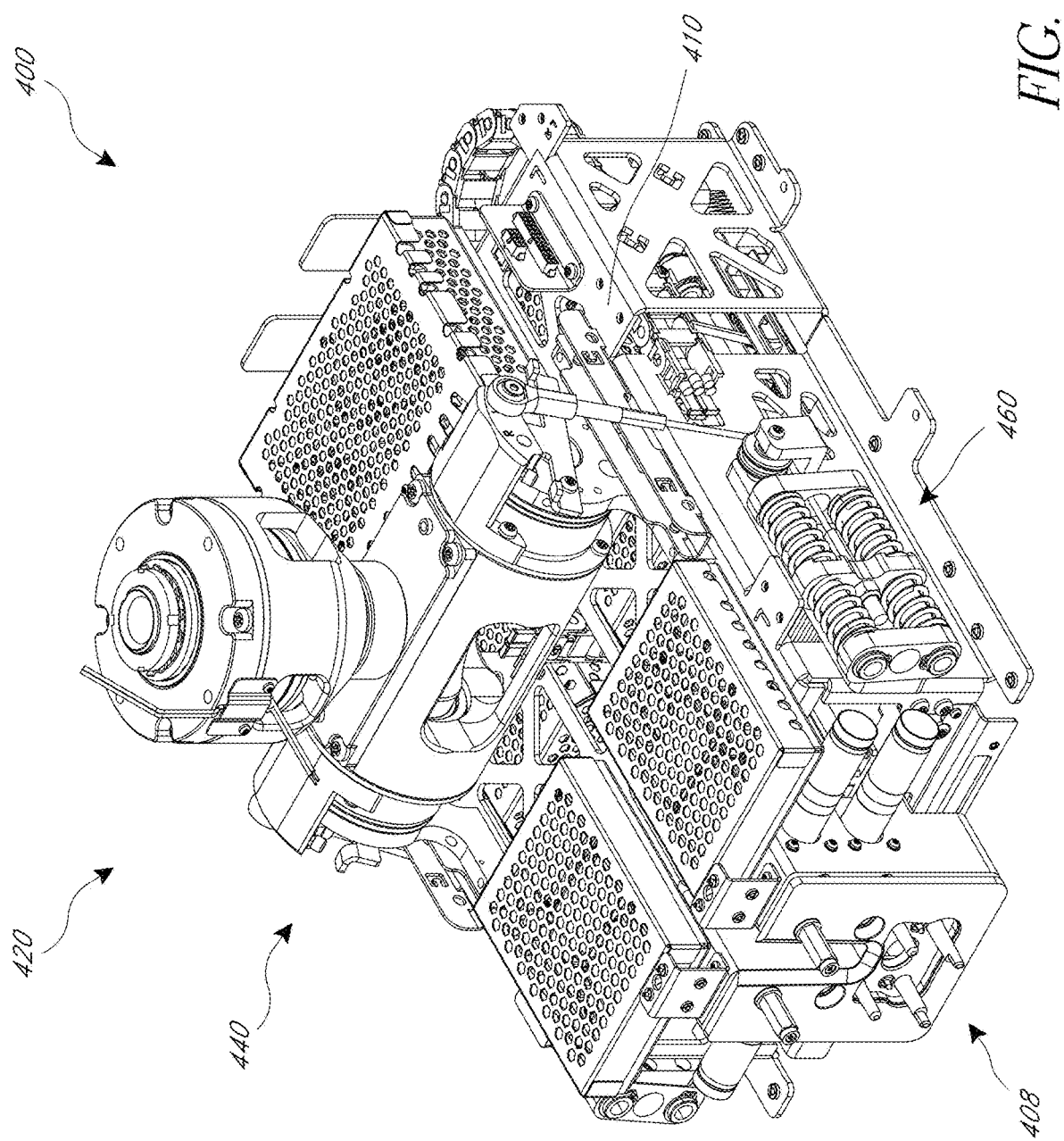
FIG. 15 is a perspective view of the control unit assembly of FIG. 14.
Figure 16:
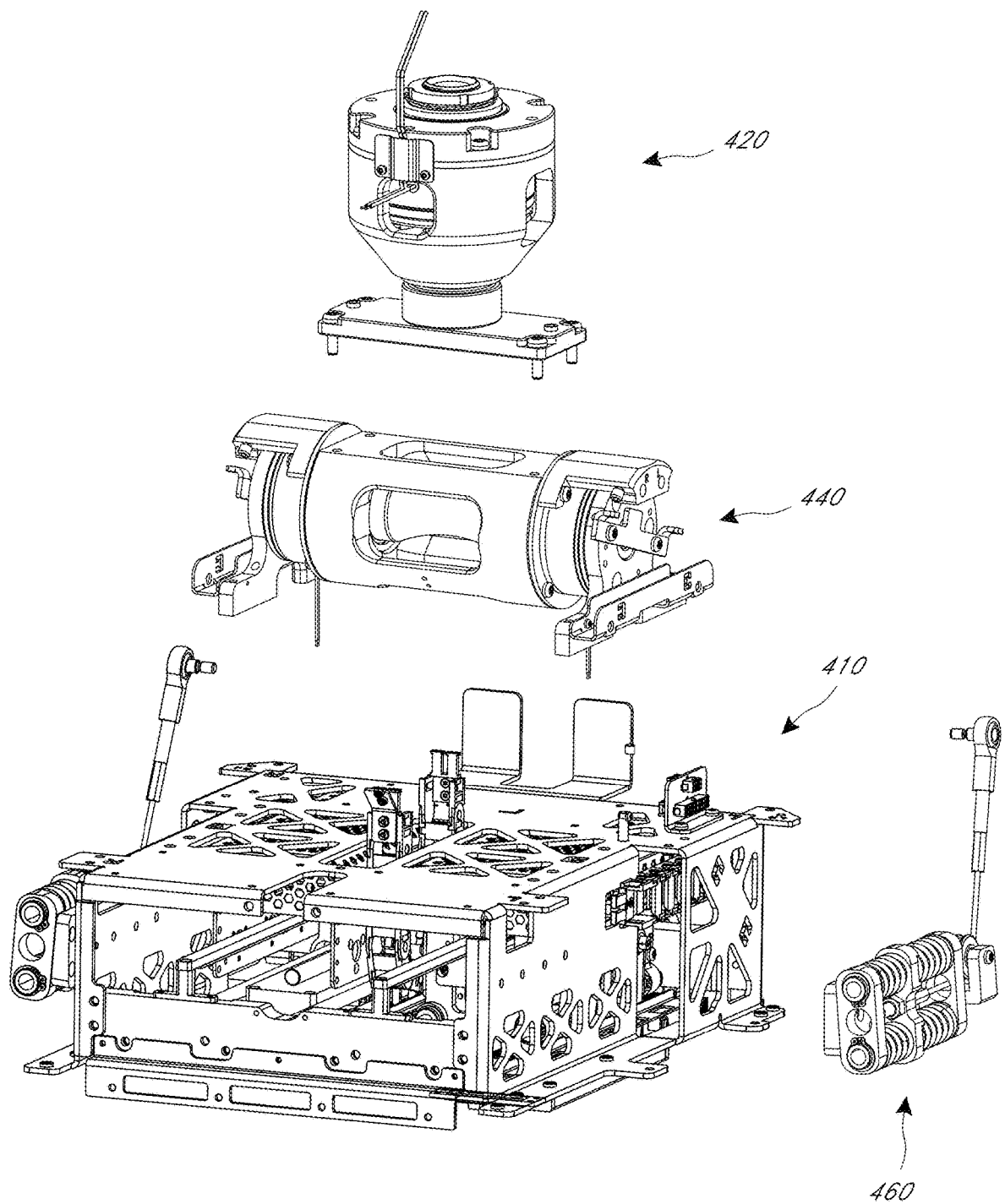
FIG. 16 is a perspective exploded view of the control unit assembly of FIG. 15.

As shown in FIGS. 15-17, the yaw control assembly 420 can be disposed above the pitch control assembly 440, so that the pitch control assembly 440 is disposed between the yaw control assembly 420 and the chassis 410. In another implementation, the pitch control assembly 440 can be disposed above the yaw control assembly 420. In still another implementation, the yaw control assembly 420 and pitch control assembly 440 can be combined and provided by a single unit. For example, the yaw control assembly 420 can pitch control assembly 440 can instead be replaced by a ball joint or spherical joint assembly that can move in a multiaxial direction and can brake independently of any axis.

As discussed above, the control unit assembly 400 can include one or more counter balance assemblies 460 (e.g., a pair of counterbalance assemblies 460A, 460B). Though the following description is for one counterbalance assembly 460, one of skill in the art will recognize that it can also apply to the other counter balance assembly 460 (e.g., the counter balance assemblies 460A, 460B are identical and mirror images of each other).

Figure 20:
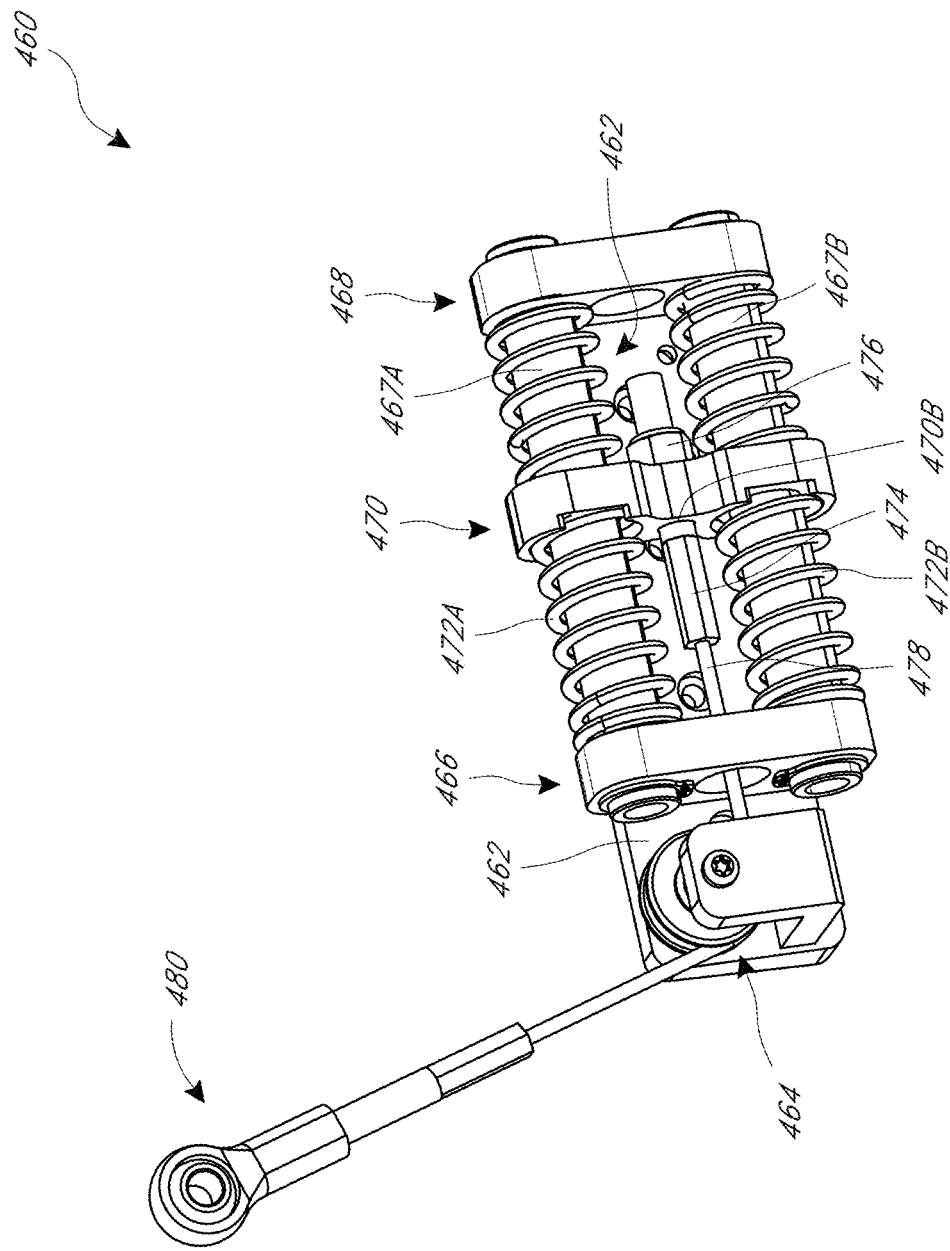
FIG. 20 is a perspective view of a counter balance assembly of the control unit assembly of FIG. 15.

With reference to FIG. 20, the counter balance assembly 460 has a base plate 462 that can be coupled to the chassis 410 (e.g., with one or more fasteners, such as screws), as shown in FIGS. 15-17. A pulley assembly 464 with one or more pulleys 464A is coupled to the base plate 462. A proximal stop cap 466 and a distal stop cap 468 can be attached to the base plate 462, with one or more (e.g., a pair of) tubes 467A, 467B extending between and interconnecting the stop caps 466, 468. One or more (e.g., a pair of) springs 472A, 472B (e.g., coil springs) can be disposed over the one or more tubes 467A, 467B. A shuttle member 470 can be disposed over the springs 472A, 472B and tubes 467A, 467B and can engage at least a portion of the springs 472A, 472B. In one implementation, the shuttle member 470 can have a pair of openings through which the tubes 467A, 467B can pass and inner wall portions (e.g., shoulders) that engage the springs 472A, 472B when the shuttle member 470 is moved (e.g., slid along the tubes 467A, 467B) relative to the springs 472A, 472B. In another implementation, a single spring can be used instead of the pair of springs 472A, 472B, but the single spring would be longer.

A shaft 474 extends through an opening 470B in the shuttle member 470 and locked relative to the shuttle member 470 (e.g., with a nut 476). A cable 478 can extend from an opposite end of the shaft 474 and wrap around the pulley 464A, extending to a proximal connector 480 (e.g., an eyelet connector). The proximal connector 480 (e.g., eyelet connector) can couple to the pitch control assembly 440 (e.g., can couple to the bracket 430, 440 of the pitch control assembly 440).

Advantageously, the counterbalance assembly 460 provides a counter balance force for the rotation of the chassis 410 during a pitch motion of the control unit assembly 400 (e.g., via the pitch control assembly 440). This advantageously contributes to the "weightlessness" of the control unit assembly 400 that is experienced by the operator by controlling the pitching motion of the chassis 410. As the chassis 410 pivots down, the springs 472A, 472B compress, and as the chassis 410 pivots up, the springs 474A, 474B decompress. The center of mass of the chassis 410 is in the rear half of the unit (e.g., at or near ¾ of the length of the chassis 410 from the front F).

In operation, the operator can actuate two user interfaces 404, 406 at the same time (e.g., generally simultaneously) to unlock one or more of (e.g., all of) the boom assembly BA, elevating linkage assembly 300, yaw control assembly 420 and pitch control assembly 440, allowing the operator to reposition the control unit assembly 400 in space (e.g., adjust a yaw and/or pitch orientation, adjust a position in space in an x-y-z Cartesian coordinate system). Advantageously, engagement of two user interfaces 404, 406 to unlock the position and/or orientation of the control unit assembly 400 allows the user to hold and/or grab the chassis 410 with both hands before the position and/or orientation is unlocked, increasing the operator's control of the control unit assembly 400. Optionally, the position and/or orientation of the control unit assembly 400 (e.g., provided by the boom assembly BA, elevating linkage assembly 300, yaw control assembly 420 and pitch control assembly 440) is not unlocked if only one user interface 404 is engaged. Once the control unit assembly has been repositioned to a desired location, the operator can lock the control unit assembly 400 in the new position by disengaging (e.g., releasing) one or both of the user interfaces 404, 406.

Additional Embodiments

In embodiments of the present invention, a robotic surgery system may be in accordance with any of the following clauses:

Clause 1. A robotic surgery system, comprising:
a control unit assembly configured to support and operate one or more robotic tools; and
a mechanical arm assembly configured to movably support the control unit assembly in space, the mechanical arm assembly comprising
a pillar assembly extending along a first axis;
a boom assembly movably coupled to the pillar assembly and extending generally perpendicular to the first axis, the boom assembly comprising a proximal boom arm rotatably coupled to the pillar assembly via a first joint and a distal boom arm rotatably coupled to the proximal boom arm via a second joint, one or more brakes arranged about one or both of the first and second joints;
an elevating linkage assembly coupled to the distal boom arm and extending along a second axis generally parallel to the first axis, the elevating linkage assembly disposed above and operatively coupled to the control unit assembly, the elevating linkage assembly comprising a brake operable to allow vertical movement of the control unit assembly relative to the boom assembly in a substantially weightless manner; and a pitch and yaw assembly disposed between the control unit assembly and the elevating linkage assembly and configured to allow movement of the control unit assembly in one or both of a pitch direction and a yaw direction, the pitch and yaw assembly comprising one or more brakes operable to substantially brake movement of the control unit assembly in one or both of pitch and yaw, wherein one or more of the brakes in the boom assembly, elevating linkage assembly and pitch and yaw assembly are actuatable between an unlocked position to allow an operator to manually change one or both of a position and an orientation of the control unit assembly in space and a locked position to fix the position and orientation of the control unit assembly in space.

Clause 2. The robotic surgery system of clause 1, wherein one or more of the brakes in the boom assembly, elevating linkage assembly and pitch and yaw assembly are electromagnetic brakes.

Clause 3. The robotic surgery system of any preceding clause, wherein the control unit assembly comprises a plurality of user interfaces configured to unlock one or more of the brakes in the boom assembly, elevating linkage assembly and pitch and yaw assembly substantially simultaneously when engaged.

Clause 4. The robotic surgery system of any clause 3, wherein the plurality of user interfaces are depressible buttons.

Clause 5. The robotic surgery system of any of clauses 3-4, wherein the plurality of user interfaces are tactile sensors.

Clause 6. The robotic surgery system of any of clauses 3-5, wherein said one or more of the brakes in the boom assembly, elevating linkage assembly and pitch and yaw assembly remain in a locked position when fewer than two user interfaces of the plurality of user interfaces are engaged.

Clause 7. The robotic surgery system of any of clauses 3-6, wherein said plurality of user interfaces are located at or proximate corners of the control unit assembly.

Clause 8. The robotic surgery system of any preceding clause, wherein the pitch and yaw assembly comprises a yaw control assembly coupled to a distal end of the elevating linkage assembly and a pitch control assembly coupled to a distal end of the yaw control assembly so that the pitch control assembly is interposed between the yaw control assembly and a chassis of the control unit assembly.

Clause 9. The robotic surgery system of clause 8, wherein the pitch control assembly extends along a third axis and the yaw control assembly extends along a fourth axis, the third and fourth axes being generally perpendicular to each other.

Clause 10. The robotic surgery system of any preceding clause, wherein the elevating linkage assembly comprises a pylon configured to move linearly relative to a frame of the elevating linkage assembly and a cable that extends from the pylon, over a pulley and couples to a compressible spring, wherein the spring exerts a spring force that substantially counteracts a force exerted on the pylon by the control unit assembly to allow movement of the control unit assembly in said substantially weightless manner.

Clause 11. The robotic surgery system of clause 10, wherein the pulley has a varying radius of curvature so that a rate of change of the spring force due to compression of the spring is substantially equal to a rate of change of the radius of the pulley such that the control unit assembly exerts substantially the same torque on the pulley during vertical motion of the control unit assembly.

Clause 12. The robotic surgery system of any preceding clause, wherein the control unit assembly comprises a counterbalance assembly comprising one or more springs compressible by a slidable shuttle, the shuttle coupled to a cable that extends over a pulley and couples to at least a portion of the pitch and yaw assembly, the cable configured to move the shuttle to compress the one or more springs during a pitch motion of the control unit assembly to counterbalance a weight of the control unit assembly to allow a pitch movement of the control unit assembly in a substantially weightless manner.

Clause 13. The robotic surgery system of any preceding clause, wherein one or more electrical cables are routed through the boom assembly and to the control unit assembly, at least a portion of the one or more cables routed via a bore in each of the first and second joints to allow rotation of the proximal and distal boom arms without entanglement of the one or more electrical cables.

Clause 14. The robotic surgery system of any preceding clause, wherein the distal boom arm is longer than the proximal boom arm, allowing the rotation of the distal boom arm over the proximal boom arm to move the control unit assembly into a stowed position.

Clause 15. A robotic surgery system, comprising:

a control unit assembly configured to support and operate one or more robotic tools; and a mechanical arm assembly configured to movably support the control unit assembly in space, the mechanical arm assembly comprising a boom assembly comprising one or more boom arms rotatably coupled to each other via one or more joints, one or more actuators arranged about the one or more joints and operable to allow movement of the one or more boom arms;

an elevating linkage assembly coupled to the boom assembly and extending along an axis generally perpendicular to the boom assembly, the elevating linkage assembly disposed above the control unit assembly and comprising an actuator operable to allow movement of the control unit assembly along the axis and relative to the boom assembly in a substantially weightless manner;

a yaw control assembly disposed below the elevating linkage assembly and above the control unit assembly, the yaw control assembly comprising an actuator operable to allow movement of the control unit assembly in a yaw direction;

a pitch control assembly disposed below the elevating linkage assembly and above the control unit assembly, the pitch control assembly comprising one or more actuators operable to allow movement of the control unit assembly in a pitch direction, wherein one or more of the actuators in the boom assembly, elevating linkage assembly, yaw control assembly and pitch control assembly are actuatable to allow a change in one or both of a position and an orientation of the control unit assembly in space upon actuation of two or more user interfaces of the control unit assembly and wherein one or more of the actuators in the boom assembly, elevating linkage assembly, yaw control assembly and pitch control assembly lock one or both of the position and the orientation of the control unit assembly when the user interfaces are not engaged.

Clause 16. The robotic surgery system of clause 15, wherein the one or more actuators in the boom assembly, elevating linkage assembly, yaw control assembly and pitch control assembly are electromagnetic brakes.

Clause 17. The robotic surgery system of any of clauses 15-16, wherein the two or more user interfaces are depressible buttons.

Clause 18. The robotic surgery system of any of clauses 15-17, wherein said actuators in the boom assembly, elevating linkage assembly, yaw control assembly and pitch control assembly lock one or both of the position and the orientation of the control unit assembly when fewer than two user interfaces are engaged.

Clause 19. The robotic surgery system of any of clauses 15-18, wherein said two or more user interfaces are located at or proximate corners of the control unit assembly.

Clause 20. The robotic surgery system of any of clauses 15-19, wherein the yaw control assembly is coupled to the elevating linkage assembly and the pitch control assembly is disposed below the yaw control assembly and coupled to a chassis of the control unit assembly.

Clause 21. The robotic surgery system of any of clauses 15-20, wherein the elevating linkage assembly comprises a pylon configured to move linearly relative to a frame of the elevating linkage assembly and a cable that extends from the pylon, over a pulley and couples to a compressible spring, wherein the spring exerts a spring force that substantially counteracts a force exerted on the pylon by the control unit assembly to allow movement of the control unit assembly in said substantially weightless manner.

Clause 22. The robotic surgery system of clause 21, wherein the pulley has a varying radius of curvature so that a rate of change of the spring force due to compression of the spring is substantially equal to a rate of change of the radius of the pulley such that the control unit assembly exerts substantially the same torque on the pulley during vertical motion of the control unit assembly.

Clause 23. The robotic surgery system of any of clauses 15-22, wherein the control unit assembly comprises a counterbalance assembly comprising one or more springs compressible by a slidable shuttle, the shuttle coupled to a cable that extends over a pulley and couples to at least a portion of the pitch control assembly, the cable configured to move the shuttle to compress the one or more springs during a pitch motion of the control unit assembly to counterbalance a weight of the control unit assembly to allow a pitch movement of the control unit assembly in a substantially weightless manner.

Other Variations

Those skilled in the art will appreciate that, in some embodiments, additional components and/or steps can be utilized, and disclosed components and/or steps can be combined or omitted. For example, although some embodiments are described in connection with a robotic surgery system, the disclosure is not so limited. Systems, devices, and methods described herein can be applicable to medical procedures in general, among other uses. As another example, certain components can be illustrated and/or described as being circular or cylindrical. In some implementations, the components can be additionally or alternatively include non-circular portions, such as portions having straight lines. As yet another example, any of the actuators described herein can include one or more motors, such as electrical motors. As yet another example, in addition to or instead of controlling tilt and/or pan of a camera, roll (or spin) can be controlled. For example, one or more actuators can be provided for controlling the spin.

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the invention.

The various illustrative blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. A robotic surgery system, comprising:
 a control unit assembly configured to support and operate one or more robotic tools; and
 a mechanical arm assembly configured to movably support the control unit assembly in space, the mechanical arm assembly comprising
  a pillar assembly extending along a first axis;
  a boom assembly movably coupled to the pillar assembly and extending generally perpendicular to the first axis, the boom assembly comprising a proximal boom arm rotatably coupled to the pillar assembly via a first joint and a distal boom arm rotatably coupled to the proximal boom arm via a second joint, one or more brakes arranged about one or both of the first and second joints;
  an elevating linkage assembly coupled to the distal boom arm and extending along a second axis generally parallel to the first axis, the elevating linkage assembly disposed above and operatively coupled to the control unit assembly, the elevating linkage assembly comprising a brake operable to allow vertical movement of the control unit assembly relative to the boom assembly; and a pitch and yaw assembly disposed between the control unit assembly and the elevating linkage assembly and configured to allow movement of the control unit assembly in one or both of a pitch direction and a yaw direction, the pitch and yaw assembly comprising one or more brakes operable to substantially brake movement of the control unit assembly in one or both of pitch and yaw, wherein the one or more of brakes in the boom assembly, the brake in the elevating linkage assembly and the one or more brakes in the pitch and yaw assembly are all actuatable between an unlocked position to allow an operator to manually change one or both of a position and an orientation of the control unit assembly in space and a locked position to fix the position and orientation of the control unit assembly in space.

2. The robotic surgery system of claim 1, wherein the one or more brakes in the boom assembly, the brake in the elevating linkage assembly and the one or more brakes in the pitch and yaw assembly are all electromagnetic brakes.

3. The robotic surgery system of claim 1, wherein the control unit assembly comprises a plurality of user interfaces configured to unlock the one or more brakes in the boom assembly, the brake in the elevating linkage assembly and the one or more brakes in the pitch and yaw assembly substantially simultaneously when engaged.

4. The robotic surgery system of claim 3, wherein the plurality of user interfaces are depressible buttons.

5. The robotic surgery system of claim 3, wherein the plurality of user interfaces are tactile sensors.

6. The robotic surgery system of claim 3, wherein the one or more of the brakes in the boom assembly, the brake in the elevating linkage assembly and the one or more brakes in the pitch and yaw assembly all remain in a locked position when fewer than two user interfaces of the plurality of user interfaces are engaged.

7. The robotic surgery system of claim 3, wherein said plurality of user interfaces are located at or proximate corners of the control unit assembly.

8. The robotic surgery system of claim 1, wherein the pitch and yaw assembly comprises a yaw control assembly coupled to a distal end of the elevating linkage assembly and a pitch control assembly coupled to a distal end of the yaw control assembly so that the pitch control assembly is interposed between the yaw control assembly and a chassis of the control unit assembly.

9. The robotic surgery system of claim 8, wherein the pitch control assembly extends along a third axis and the yaw control assembly extends along a fourth axis, the third and fourth axes being generally perpendicular to each other.

10. The robotic surgery system of claim 1, wherein the elevating linkage assembly comprises a pylon configured to move linearly relative to a frame of the elevating linkage assembly and a cable that extends from the pylon, over a pulley and couples to a compressible spring, wherein the spring exerts a spring force that substantially counteracts a force exerted on the pylon by the control unit assembly to allow movement of the control unit assembly in a substantially weightless manner.

11. The robotic surgery system of claim 10, wherein the pulley has a varying radius of curvature so that a rate of change of the spring force due to compression of the spring is substantially equal to a rate of change of the radius of the pulley such that the control unit assembly exerts substantially the same torque on the pulley during vertical motion of the control unit assembly.

12. The robotic surgery system of claim 1, wherein the control unit assembly comprises a counterbalance assembly comprising one or more springs compressible by a slidable shuttle, the shuttle coupled to a cable that extends over a pulley and couples to at least a portion of the pitch and yaw assembly, the cable configured to move the shuttle to compress the one or more springs during a pitch motion of the control unit assembly to counterbalance a weight of the control unit assembly to allow a pitch movement of the control unit assembly in a substantially weightless manner.

13. The robotic surgery system of claim 1, wherein one or more electrical cables are routed through the boom assembly and to the control unit assembly, at least a portion of the one or more cables routed via a bore in each of the first and second joints to allow rotation of the proximal and distal boom arms without entanglement of the one or more electrical cables.

14. The robotic surgery system of claim 1, wherein the distal boom arm is longer than the proximal boom arm, allowing the rotation of the distal boom arm over the proximal boom arm to move the control unit assembly into a stowed position.

15. A robotic surgery system, comprising:
a control unit assembly configured to support and operate one or more robotic tools; and
a mechanical arm assembly configured to movably support the control unit assembly in space, the mechanical arm assembly comprising
a boom assembly comprising one or more boom arms rotatably coupled to each other via one or more joints, one or more actuators arranged about the one or more joints and operable to allow movement of the one or more boom arms;
an elevating linkage assembly coupled to the boom assembly and extending along an axis generally perpendicular to the boom assembly, the elevating linkage assembly disposed above the control unit assembly and comprising an actuator operable to allow movement of the control unit assembly along the axis and relative to the boom assembly;
a yaw control assembly disposed below the elevating linkage assembly and above the control unit assembly, the yaw control assembly comprising an actuator operable to allow movement of the control unit assembly in a yaw direction;
a pitch control assembly disposed below the elevating linkage assembly and above the control unit assembly, the pitch control assembly comprising one or more actuators operable to allow movement of the control unit assembly in a pitch direction,
wherein the one or more actuators in the boom assembly, the actuator in the elevating linkage assembly, the actuator in the yaw control assembly and the one or more actuators in the pitch control assembly are all actuatable to allow a change in one or both of a position and an orientation of the control unit assembly in space upon actuation of two or more user interfaces of the control unit assembly and wherein the one or more actuators in the boom assembly, the actuator in the elevating linkage assembly, the actuator in the yaw control assembly and the one or more actuators in the pitch control assembly lock one or both of the position and the orientation of the control unit assembly when the user interfaces are not engaged.

16. The robotic surgery system of claim 15, wherein the one or more actuators in the boom assembly, the actuator in the elevating linkage assembly, the actuator in the yaw control assembly and the one or more actuators in the pitch control assembly are all electromagnetic brakes.

17. The robotic surgery system of claim 15, wherein the two or more user interfaces are depressible buttons.

18. The robotic surgery system of claim 15, wherein the one or more actuators in the boom assembly, the actuator in the elevating linkage assembly, the actuator in the yaw control assembly and one or more actuators in the pitch control assembly lock one or both of the position and the orientation of the control unit assembly when fewer than two user interfaces are engaged.

19. The robotic surgery system of claim 15, wherein said two or more user interfaces are located at or proximate corners of the control unit assembly.

20. The robotic surgery system of claim 15, wherein the yaw control assembly is coupled to the elevating linkage assembly and the pitch control assembly is disposed below the yaw control assembly and coupled to a chassis of the control unit assembly.

21. The robotic surgery system of claim 15, wherein the elevating linkage assembly comprises a pylon configured to move linearly relative to a frame of the elevating linkage assembly and a cable that extends from the pylon, over a pulley and couples to a compressible spring, wherein the spring exerts a spring force that substantially counteracts a force exerted on the pylon by the control unit assembly to allow movement of the control unit assembly in a substantially weightless manner.

22. The robotic surgery system of claim 21, wherein the pulley has a varying radius of curvature so that a rate of change of the spring force due to compression of the spring is substantially equal to a rate of change of the radius of the pulley such that the control unit assembly exerts substantially the same torque on the pulley during vertical motion of the control unit assembly.

23. The robotic surgery system of claim 15, wherein the control unit assembly comprises a counterbalance assembly comprising one or more springs compressible by a slidable shuttle, the shuttle coupled to a cable that extends over a pulley and couples to at least a portion of the pitch control assembly, the cable configured to move the shuttle to compress the one or more springs during a pitch motion of the control unit assembly to counterbalance a weight of the control unit assembly to allow a pitch movement of the control unit assembly in a substantially weightless manner.

* * * * *